United States Patent
Lacrampe et al.

(10) Patent No.: US 8,088,795 B2
(45) Date of Patent: Jan. 3, 2012

(54) CYCLIC-ALKYLAMINE DERIVATIVES AS INHIBITORS OF THE INTERACTION BETWEEN MDM2 AND P53

(75) Inventors: Jean Fernand Armand Lacrampe, Le Mesnil-Esnard (FR); Christophe Meyer, Les Authieux sur le Port Saint Ouen (FR); Bruno Schoentjes, Bois-Guillaume (FR); Alain Philippe Poncelet, Le Manoir sur Seine (FR); Camille Georges Wermuth, Strasbourg (FR); Bruno Giethlen, Altorf (FR); Jean-Marie Contreras, Benfeld (FR); Muriel Joubert, Illkirch (FR); Luc Van Hijfte, Belbeuf (FR)

(73) Assignee: Janssen Pharmaceutica N.V., Beerse (BE)

(*) Notice: Subject to any disclaimer, the term of this patent is extended or adjusted under 35 U.S.C. 154(b) by 228 days.

(21) Appl. No.: 12/293,566

(22) PCT Filed: Mar. 19, 2007

(86) PCT No.: PCT/EP2007/052582
§ 371 (c)(1),
(2), (4) Date: Sep. 19, 2008

(87) PCT Pub. No.: WO2007/107545
PCT Pub. Date: Sep. 27, 2007

(65) Prior Publication Data
US 2010/0168163 A1    Jul. 1, 2010

Related U.S. Application Data

(60) Provisional application No. 60/785,120, filed on Mar. 23, 2006.

(51) Int. Cl.
A61K 31/4709 (2006.01)
A61K 31/4439 (2006.01)
C07D 401/14 (2006.01)
A61P 35/00 (2006.01)

(52) U.S. Cl. .............. 514/313; 514/339; 546/277.4; 546/160

(58) Field of Classification Search .......... None
See application file for complete search history.

(56) References Cited

U.S. PATENT DOCUMENTS
7,122,547 B1  10/2006  Huth et al.

FOREIGN PATENT DOCUMENTS

| | | |
|---|---|---|
| EP | 1129074 | 5/2000 |
| EP | 1137418 | 6/2000 |
| EP | 1379239 | 9/2007 |
| EP | 1519932 | 10/2007 |
| EP | 1458380 | 3/2008 |
| EP | 1443937 | 6/2008 |
| EP | 1317443 | 1/2009 |
| JP | 11130750 | 5/1999 |
| WO | 0015357 | 3/2003 |
| WO | 0015657 | 3/2003 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995.*
Horig et al. Journal of Translational Medicine 2004, 2(44).*
Schafer et al. Drug Discovery Today 2008, 13 (21/22), 913-916.*
Vousden, K.H., "p53 Death Star" Cell, vol. 103, pp. 691-694 (2000).
Finney, D.J., "Graded Responses" Probit Analysis, A Statistical Treatment of The Sigmoid Response Curve, $2^{nd}$ Edition, Chapter 10, Cambridge University (1962).

* cited by examiner

Primary Examiner — Timothy Thomas
Assistant Examiner — Dennis Heyer
(74) Attorney, Agent, or Firm — Rajiv S. Shah

(57) ABSTRACT

The present invention provides compounds of formula (I), their use as an inhibitor of a p53-MDM2 interaction as well as pharmaceutical compositions comprising said compounds of formula (I) wherein n, m, p, t, $R^1$, $R^2$, $R^3$, $R^4$, $R^5$, $R^6$, $R^7$, Q, Y and Z have defined meanings.

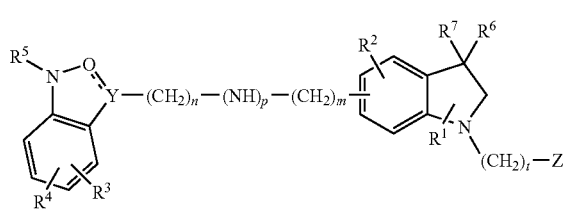

(I)

6 Claims, No Drawings

US 8,088,795 B2

CYCLIC-ALKYLAMINE DERIVATIVES AS INHIBITORS OF THE INTERACTION BETWEEN MDM2 AND P53

CROSS REFERENCE TO RELATED APPLICATIONS

This application is the national stage of PCT Application No. PCT/EP2007/052582, filed Mar. 19, 2007, which claims priority from European Patent Application No. 06111529.1, filed Mar. 22, 2006, and U.S. Provisional Patent Application No. 60/785,120, filed Mar. 23, 2006, the entire disclosures of which are hereby incorporated in their entirely.

FIELD OF THE INVENTION

The present invention relates to compounds and compositions containing said compounds acting as inhibitors of the interaction between MDM2 and p53. Moreover, the present invention provides processes for the preparation of the disclosed inhibitors, compositions comprising them and methods of using them, for instance as a medicine.

p53 is a tumour suppressor protein which plays a pivotal role in the regulation of the balance between cell proliferation and cell growth arrest/apoptosis. Under normal conditions the half life of p53 is very short and consequently the level of p53 in cells is low. However, in response to cellular DNA damage or cellular stress (e.g. oncogene activation, telomere erosion, hypoxia), levels of p53 increase. This increase in p53 levels leads to the activation of the transcription of a number of genes which drives the cell into either growth arrest or into the processes of apoptosis. Thus, an important function of p53 is to prevent the uncontrolled proliferation of damaged cells and thus protect the organism from the development of cancer.

MDM2 is a key negative regulator of p53 function. It forms a negative autoregulatory loop by binding to the amino terminal transactivation domain of p53 and thus MDM2 both inhibits the ability of p53 to activate transcription and targets p53 for proteolytic degradation. Under normal conditions this regulatory loop is responsible for maintaining the low levels of p53. However, in tumours with wild-type p53, the equilibrium concentration of active p53 can be increased by antagonising the interaction between MDM2 and p53. This will result in restoration of the p53-mediated pro-apoptotic and anti-proliferative effects in such tumour cells.

MDM2 is a cellular proto-oncogene. Over-expression of MDM2 has been observed in a range of cancers. MDM2 is over-expressed in a variety of tumours due to gene amplification or increased transcription or translation. The mechanism by which MDM2 amplification promotes tumourigenesis is at least in part related to its interaction with p53. In cells over-expressing MDM2 the protective function of p53 is blocked and thus cells are unable to respond to DNA damage or cellular stress by increasing p53 levels, leading to cell growth arrest and/or apoptosis. Thus after DNA damage and/or cellular stress, cells over-expressing MDM2 are free to continue to proliferate and assume a tumorigenic phenotype. Under these conditions disruption of the interaction of p53 and MDM2 would release the p53 and thus allow normal signals of growth arrest and/or apoptosis to function.

MDM2 may also have separate functions in addition to inhibition of p53. For example, it has been shown that MDM2 interacts directly with the pRb-regulated transcription factor E2F1/DP1. This interaction could be crucial for the p53-independent oncogenic activities of MDM2. A domain of E2F1 shows striking similarity to the MDM2-binding domain of p53. Since the interactions of MDM2 with both p53 and E2F1 locate to the same binding site on MDM2, it can be expected that MDM2/p53 antagonists will not only activate cellular p53 but also modulate E2F1 activities, which are commonly deregulated in tumour cells.

Also the therapeutic effectiveness of DNA damaging agents currently used (chemotherapy and radiotherapy), may be limited through the negative regulation of p53 by MDM2. Thus if the MDM2 feed-back inhibition of p53 is interrupted, an increase in functional p53 levels will increase the therapeutic effectiveness of such agents by restoring the wild-type p53 function that leads to apoptosis and/or reversing of p53-associated drug resistance. It was demonstrated that combining MDM2 inhibition and DNA-damaging treatments in vivo led to synergistic anti-tumour effects (Vousden K. H., Cell, Vol. 103, 691-694, 2000).

Thus disruption of the interaction of MDM2 and p53 offers an approach for therapeutic intervention in tumours with wild-type p53, might even exhibit anti-proliferative effects in tumour cells that are devoid of functional p53 and furthermore can sensitise tumorigenic cells for chemotherapy and radiotherapy.

BACKGROUND OF THE INVENTION

JP 11130750, published on 18 May 1999, describes amongst others, substituted phenylaminocarbonylindolyl derivatives as 5-HT receptor antagonists.

EP1129074, published on 18 May 2000, describes anthranilic acid amides as inhibitors of vascular endothelial growth factor receptors (VEGFR) and useful in the treatment of angiogenic disorders.

EP1317443, published on 21 Mar. 2002, discloses tricyclic tert-amine derivatives, useful as chemokine receptor CXCR4 or CCR5 modulators for treating human immunodeficiency virus and feline immunodeficiency virus.

EP1379239, published on 10 Oct. 2002, discloses N-(2-arylethyl)benzylamines as antagonists of the 5-HT$_6$ receptor.

WO00/15357, published on 23 Mar. 2000, provides piperazine-4-phenyl derivatives as inhibitors of the interaction between MDM2 and p53. EP1137418, published on 8 Jun. 2000, provides tricyclic compounds for restoring conformational stability of a protein of the p53 family.

EP1443937, published on 22 May 2003, describes substituted 1,4-benzodiazepines and the uses thereof as inhibitors of the MDM2-p53 interactions.

EP1458380, published on 26 Jun. 2003, provides cis-2,4,5-triphenyl-imidazolones that inhibit the interaction of MDM2 protein with p53-like peptides and have antiproliferative activity.

EP1519932, published on 15 Jan. 2004, discloses bisaryl-sulfonamide compounds that bind to MDM2 and can be used in cancer therapy.

There continues to be a need for effective and potent small molecules that inhibit the interactions between MDM2 and p53.

The compounds of the present invention differs from the prior art in structure, in their pharmacological activity and/or in pharmacological potency.

DESCRIPTION OF THE INVENTION

The present invention provides compounds, compositions for, and methods of, inhibiting the interactions between MDM2 and p53 for treating cancer. Furthermore the compounds and compositions of the present invention are useful in enhancing the effectiveness of chemotherapy and radiotherapy.

This invention concerns compounds of formula (I)

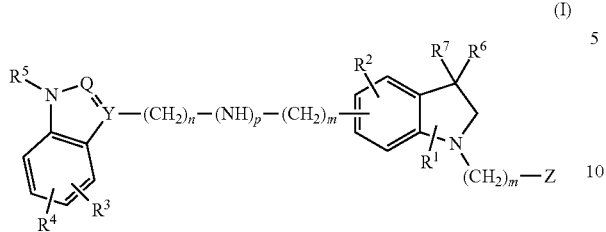

a N-oxide form, an addition salt or a stereochemically isomeric form thereof, wherein
m is 0, 1, or 2 and when m is 0 then a direct bond is intended;
n is 0, 1, 2, or 3 and when n is 0 then a direct bond is intended;
p is 0, or 1 and when p is 0 then a direct bond is intended;
t is 0 or 1 and when t is 0 then a direct bond is intended;

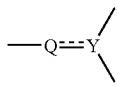

is —CR$^8$=C< and then the dotted line is a bond, —C(=O)—CH<, —C(=O)—N<, —CHR$^8$—CH< or —CHR$^8$—N<; wherein
  each R$^8$ is independently hydrogen or C$_{1-6}$alkyl;
R$^1$ and R$^2$ are each independently selected from hydrogen, halo, C$_{1-6}$alkyl, C$_{1-6}$alkyloxy, arylC$_{1-6}$alkyloxy, heteroarylC$_{1-6}$alkyloxy, phenylthio, hydroxyC$_{1-6}$alkylcarbonyl, C$_{1-6}$alkyl substituted with a substituent selected from amino, aryl and heteroaryl; or C$_{3-7}$cycloalkyl substituted with a substituent selected from amino, aryl and heteroaryl;
R$^3$ and R$^4$ are each independently selected from hydrogen, halo, C$_{1-6}$alkyl, polyhaloC$_{1-6}$alkyl, cyano, cyanoC$_{1-6}$alkyl, hydroxy, amino or C$_{1-6}$alkyloxy; or
R$^4$ and R$^5$ together can optionally form a bivalent radical selected from methylenedioxy or ethylenedioxy;
R$^5$ is hydrogen, C$_{1-6}$alkyloxycarbonyl or C$_{1-6}$alkyl;
R$^6$ and R$^7$ are each independently selected from hydrogen, C$_{1-6}$alkyloxyC$_{1-6}$alkyl or C$_{1-6}$alkyl; or
R$^6$ and R$^7$ together can optionally form a bivalent radical selected from —(CH$_2$)$_2$—O—(CH$_2$)$_2$—     (b-1)

—(CH$_2$)$_2$—NR$^9$—(CH$_2$)$_2$—     (b-2)

wherein R$^9$ is hydrogen, C$_{1-6}$alkyloxyC$_{1-6}$alkyl or C$_{1-6}$alkyl;
Z is a radical selected from

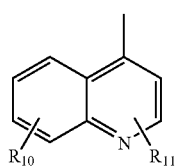
(a-1)

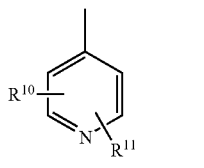
(a-2)

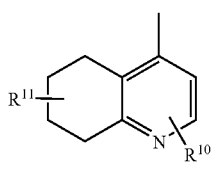
(a-3)

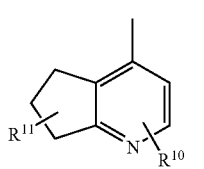
(a-4)

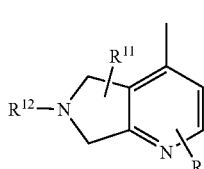
(a-5)

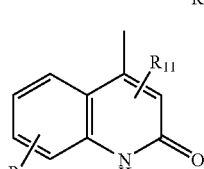
(a-6)

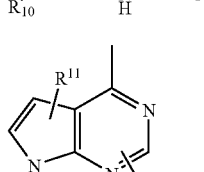
(a-7)

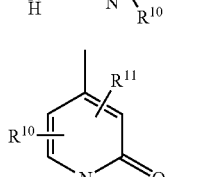
(a-8)

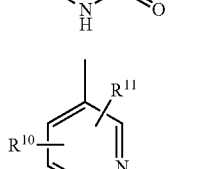
(a-9)

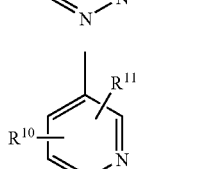
(a-10)

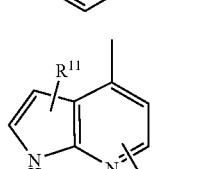
(a-11)

(a-12)

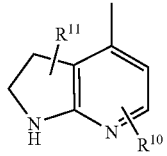

wherein
$R^{10}$ and $R^{11}$ are each independently selected from hydrogen, halo, hydroxy, amino, $C_{1-6}$alkyl, nitro, polyhalo$C_{1-6}$alkyl, cyano, cyano$C_{1-6}$alkyl, tetrazolo$C_{1-6}$alkyl, aryl, heteroaryl, aryl$C_{1-6}$alkyl, heteroaryl$C_{1-6}$alkyl, aryl(hydroxy)$C_{1-6}$allyl, heteroaryl(hydroxy)$C_{1-6}$alkyl, arylcarbonyl, heteroarylcarbonyl, $C_{1-6}$alkylcarbonyl, aryl$C_{1-6}$alkylcarbonyl, heteroaryl$C_{1-6}$alkylcarbonyl, $C_{1-6}$alkyloxy, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$allyl, $C_{1-6}$alkyloxycarbonyl$C_{2-6}$alkenyl $C_{1-6}$alkyloxy$C_{1-6}$alkyl, $C_{1-6}$alkyloxycarbonyl, $C_{1-6}$alkylcarbonyloxy, aminocarbonyl, hydroxy$C_{1-6}$alkyl, amino$C_{1-6}$alkyl, hydroxycarbonyl, hydroxycarbonyl$C_{1-6}$allyl and —$(CH_2)_v$—$(C(=O)_r)$—$(CHR^{17})_u$—$NR^{13}R^{14}$; wherein
v is 0, 1, 2, 3, 4, 5, or 6 and when v is 0 then a direct bond is intended;
r is 0, or 1 and when r is 0 then a direct bond is intended;
u is 0, 1, 2, 3, 4, 5, or 6 and when u is 0 then a direct bond is intended;
$R^{17}$ is hydrogen or $C_{1-6}$alkyl;
$R^{12}$ is hydrogen, $C_{1-6}$allyl, $C_{3-7}$cycloalkyl, $C_{1-6}$alkyl substituted with a substituent selected from hydroxy, amino, $C_{1-6}$alkyloxy and aryl; or $C_{3-7}$cycloalkyl substituted with a substituent selected from hydroxy, amino, aryl and $C_{1-6}$alkyloxy;
$R^{13}$ and $R^{14}$ are each independently selected from hydrogen, $C_{1-12}$alkyl, $C_{1-6}$alkylcarbonyl, $C_{1-6}$alkylsulfonyl, aryl$C_{1-6}$alkylcarbonyl, $C_{3-7}$cycloalkyl, $C_{3-7}$cycloalkylcarbonyl, —$(CH_2)_k$—$NR^{15}R^{16}$, $C_{1-12}$alkyl substituted with a substituent selected from hydroxy, hydroxycarbonyl, cyano, $C_{1-6}$alkyloxycarbonyl, $C_{1-6}$alkyloxy, aryl or heteroaryl; or $C_{3-7}$cycloalkyl substituted with a substituent selected from hydroxy, $C_{1-6}$alkyloxy, aryl, amino, aryl$C_{1-6}$alkyl, heteroaryl or heteroaryl$C_{1-6}$alkyl; or
$R^{13}$ and $R^{14}$ together with the nitrogen to which they are attached can optionally form a morpholinyl, piperidinyl, pyrrolidinyl, piperazinyl, or piperazinyl substituted with a substituent selected from $C_{1-6}$alkyl, aryl$C_{1-6}$alkyl, aryl$C_{1-6}$alkyloxycarbonyl, heteroaryl$C_{1-6}$alkyl, $C_{3-7}$cycloalkyl and $C_{3-7}$cycloalkyl$C_{1-6}$alkyl; wherein
k is 0, 1, 2, 3, 4, 5, or 6 and when k is 0 then a direct bond is intended;
$R^{15}$ and $R^{16}$ are each independently selected from hydrogen, $C_{1-6}$alkyl, aryl$C_{1-6}$alkyloxycarbonyl, $C_{3-7}$cycloalkyl, $C_{1-12}$alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl, and heteroaryl$C_{1-6}$alkyl; or
$R^{15}$ and $R^{16}$ together with the nitrogen to which they are attached can optionally form a morpholinyl, a piperazinyl or a piperazinyl substituted with $C_{1-6}$alkyloxycarbonyl;

aryl is phenyl or naphthalenyl;
each phenyl or naphthalenyl can optionally be substituted with one, two or three substituents each independently selected from halo, hydroxy, $C_{1-6}$alkyl, amino, polyhalo$C_{1-6}$alkyl and $C_{1-6}$alkyloxy; and
each phenyl or naphthalenyl can optionally be substituted with a bivalent radical selected from methylenedioxy and ethylenedioxy;
heteroaryl is pyridinyl, indolyl, quinolinyl, imidazolyl, furanyl, thienyl, oxadiazolyl, tetrazolyl, benzofuranyl or tetrahydrofuranyl;
each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently selected from halo, hydroxy, $C_{1-6}$alkyl, amino, polyhalo$C_{1-6}$alkyl, aryl, aryl$C_{1-6}$alkyl or $C_{1-6}$alkyloxy; and
each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy.

The compounds of formula (I) may also exist in their tautomeric forms. Such forms although not explicitly indicated in the above formula are intended to be included within the scope of the present invention.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; $C_{1-6}$alkyl defines straight and branched chain saturated hydrocarbon radicals having from 1 to 6 carbon atoms such as, e.g. methyl, ethyl, propyl, butyl, pentyl, hexyl, 1-methylethyl, 2-methylpropyl, 2-methyl-butyl, 2-methylpentyl and the like; hydroxy$C_{1-6}$alkyl defines a hydroxy substituent on straight and branched chain saturated hydrocarbon radicals having from 1 to 6 carbon atoms; trihalomethyl defines methyl containing three identical or different halo substituents for example trifluoromethyl; $C_{3-7}$cycloalkyl includes cyclic hydrocarbon groups having from 3 to 10 carbons, such as cyclopropyl, cyclobutyl, cyclopentyl, cyclopentenyl, cyclohexyl, cyclohexenyl, cycloheptyl, and the like.

The term "addition salt" comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

The term "addition salt" further comprises pharmaceutically acceptable salts, metal complexes and solvates and the salts thereof, that the compounds of formula (I) are able to form.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

The term "metal complexes" means a complex formed between a compound of formula (I) and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like.

The term "stereochemically isomeric forms of compounds of formula (I)", as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Of special interest are those compounds of formula (I) which are stereo chemically pure.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

The tautomeric forms of the compounds of formula (I) are meant to comprise those compounds of formula (I) wherein e.g. an enol group is converted into a keto group (keto-enol tautomerism).

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The present invention is also intended to include any isotopes of atoms present in the compounds of the invention. For example, isotopes of hydrogen include tritium and deuterium and isotopes of carbon include C-13 and C-14.

Whenever used hereinafter, the term "compounds of formula (I)" is meant to include also the N-oxide forms, the pharmaceutically acceptable acid or base addition salts and all stereoisomeric forms.

A first group of interesting compounds consists of those compounds of formula (I) wherein one or more of the following restrictions apply:

a) m is 0;

b) n is 2;

c) p is 1;

d) t is 0;

e) 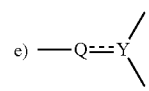

is —CH=C<;

f) $R^1$ and $R^2$ are each independently hydrogen;

g) $R^3$ and $R^4$ are each independently hydrogen;

h) $R^5$ is hydrogen;

i) $R^6$ and $R^7$ are each independently hydrogen or $C_{1-6}$alkyl;

j) Z is a radical selected from (a-1), (a-2) or (a-4); or k) $R^{10}$ and $R^{11}$ are each independently selected from hydrogen, hydroxy, $C_{1-6}$alkyloxycarbonyl or hydroxy$C_{1-6}$alkyl.

A second group of interesting compounds consists of those compounds of formula (I) and those compounds of the first group of interesting compounds wherein one or more of the following restrictions apply:
a) m is 0;
b) n is 2;
c) p is 1;
d) t is 0;

e) 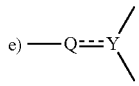 is —CH=C<;

f) $R^1$ and $R^2$ are each independently hydrogen;
g) $R^3$ and $R^4$ are each independently hydrogen;
h) $R^5$ is hydrogen;
i) $R^6$ and $R^7$ are each independently hydrogen.
j) Z is a radical selected from (a-2) or (a-4); or
k) $R^{10}$ and $R^{11}$ are each independently selected from hydrogen, hydroxy, or hydroxy$C_{1-6}$alkyl.

A group of preferred compounds consists of those compounds of formula (I) or any subgroup thereof; wherein m is 0; n is 0; p is 1; t is 0; $R^1$ and $R^2$ are each independently hydrogen; $R^3$ and $R^4$ are each independently hydrogen; $R^5$ is hydrogen; $R^6$ and $R^7$ are each independently hydrogen or $C_{1-6}$alky; Z is a radical selected from (a-1), (a-2) or (a-4); or $R^{10}$ and $R^{11}$ are each independently selected from hydrogen, hydroxy, $C_{1-6}$alkyloxycarbonyl or hydroxy$C_{1-6}$alkyl.

A group of more preferred compounds consists of those compounds of formula (I) or any subgroup thereof wherein m is 0; n is 0; p is 1; t is 0; $R^1$ and $R^2$ are each independently hydrogen; $R^3$ and $R^4$ are each independently hydrogen; $R^5$ is hydrogen; $R^6$ and $R^7$ are each independently hydrogen; Z is a radical selected from (a-2) or (a-4); or $R^{10}$ and $R^{11}$ are each independently selected from hydrogen, hydroxy, or hydroxy$C_{1-6}$allyl.

The most preferred compounds are compound No. 1, compound No. 4 and compound No. 5.

Co. No. 1
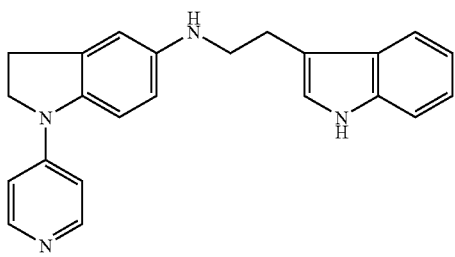

Co. No. 4
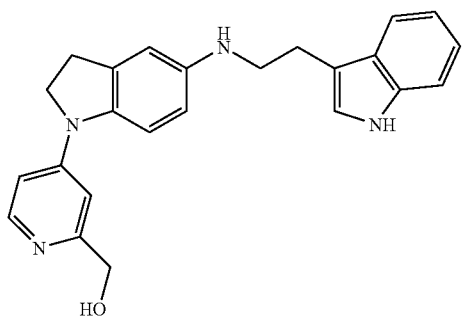

Co. No. 5
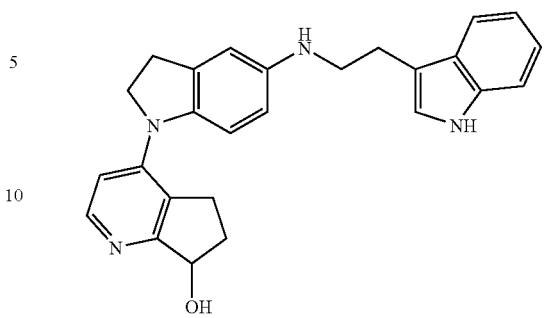

The compounds of formula (I), their pharmaceutically acceptable salts and N-oxides and stereochemically isomeric forms thereof may be prepared in conventional manner. The starting materials and some of the intermediates are known compounds and are commercially available or may be prepared according to conventional reaction procedures as generally known in the art.

A number of such preparation methods will be described hereinafter in more detail. Other methods for obtaining final compounds of formula (I) are described in the examples.

The compounds of formula (I) can be prepared by reacting an intermediate of formula (II) with an intermediate of formula (III) wherein W is an appropriate leaving group such as, for example, halo, e.g. fluoro, chloro, bromo or iodo, or a sulfonyloxy radical such as methylsulfonyloxy, 4-methylphenylsulfonyloxy and the like. The reaction can be performed in a reaction-inert solvent such as, for example, an alcohol, e.g. methanol, ethanol, 2-methoxy-ethanol, propanol, butanol and the like; an ether, e.g. 4,4-dioxane, 1,1'-oxybispropane and the like; a ketone, e.g. 4-methyl-2-pentanone; or N,N-dimethylformamide, nitrobenzene, acetonitrile, acetic acid and the like. The addition of an appropriate base such as, for example, an alkali or earth alkaline metal carbonate or hydrogen carbonate, e.g. triethylamine or sodium carbonate, may be utilized to pick up the acid which is liberated during the course of the reaction. A small amount of an appropriate metal iodide, e.g., sodium or potassium iodide may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

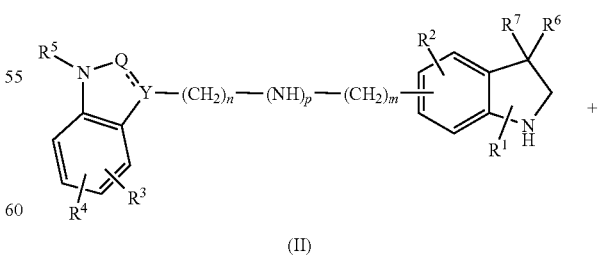

(II)

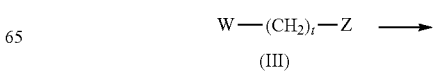

(III)

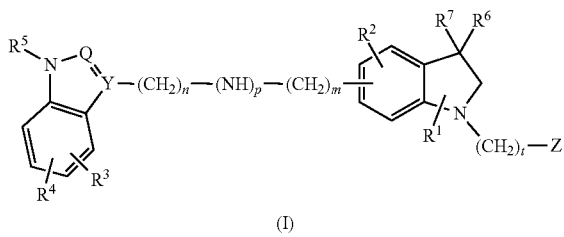

(I)

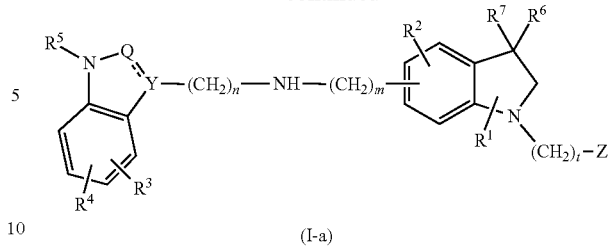

(I-a)

The compounds of formula (I), wherein p is 1, herein referred to as compounds of formula (I-a) can be prepared by converting intermediates of formula (IV) with lithium aluminium hydride in a suitable solvent such as tetrahydrofuran.

In an identical way the compounds of formula (I), wherein t is 1, herein referred to as compounds of formula (I-b), can be prepared by reacting an intermediate of formula (II) with an appropriate carboxaldehyde of formula (VII).

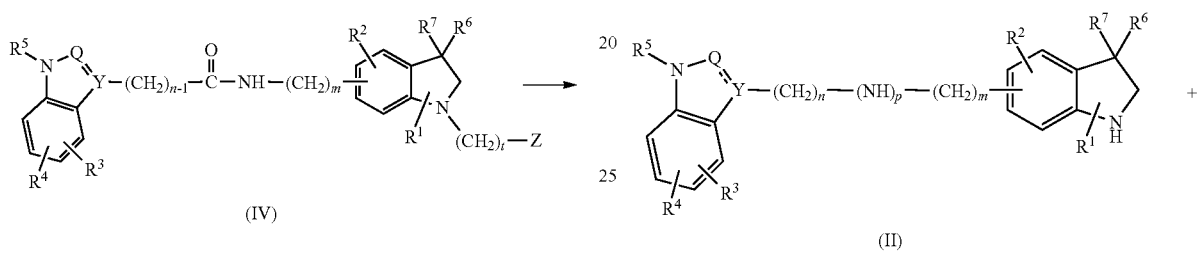

(IV)

(I-a)

The compounds of formula (I-a) can also be prepared by reacting an appropriate carboxaldehyde of formula (VI), with an intermediate of formula (V), in the presence of an appropriate reagent, such as a sodium borohydride e.g. sodium tetrahydroborate or polymer supported cyanotrihydroborate, in a suitable solvent, such as an alcohol e.g. methanol.

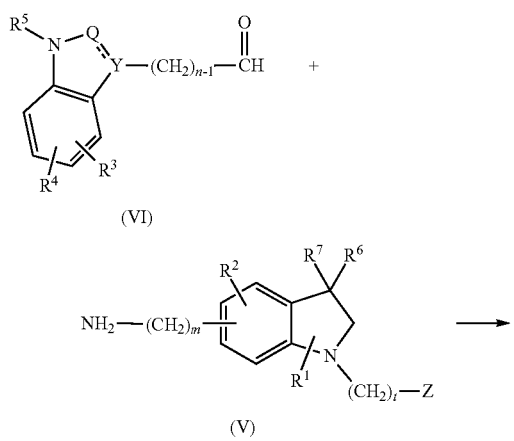

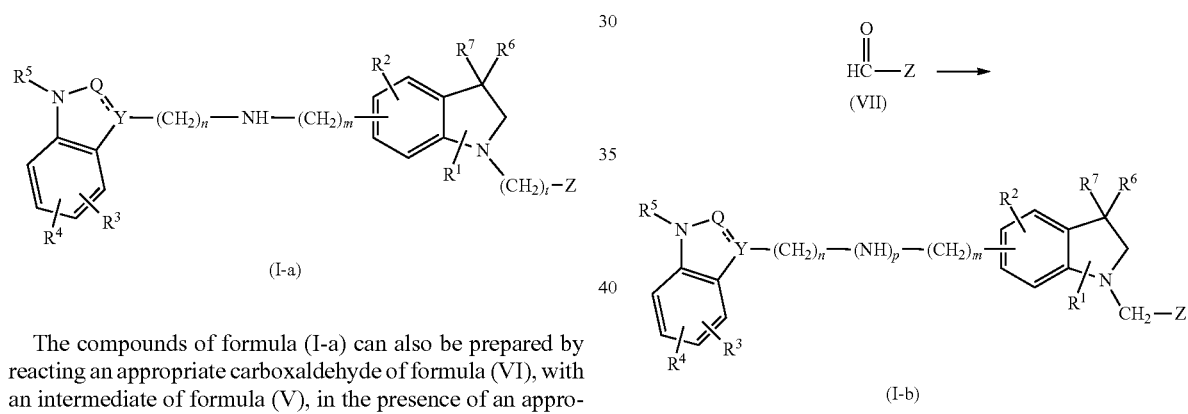

(II)

(VII)

(I-b)

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

The intermediates of formula (V) wherein m is 0, herein referred to as intermediates of formula (V-a), can be prepared by converting an intermediate of formula (VIII) with hydrazine hydrate in a suitable solvent such as methanol.

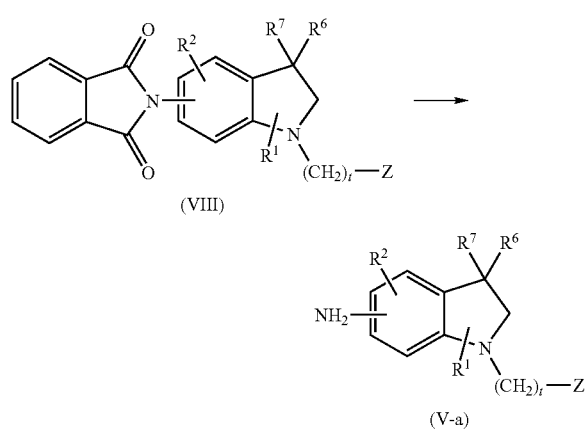

(VIII)

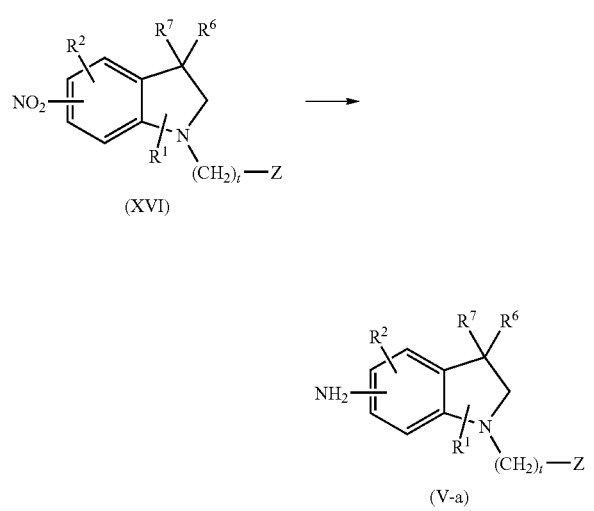

(V-a)

Intermediates of formula (V-a), can also be prepared by a nitro to amine reduction reaction starting with an intermediate of formula (XVI), in the presence of a metal catalyst such as Raney Nickel and an appropriate reductant such as hydrogen, in a suitable solvent such as methanol or ethanol.

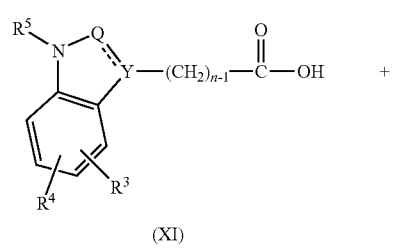

(XVI)

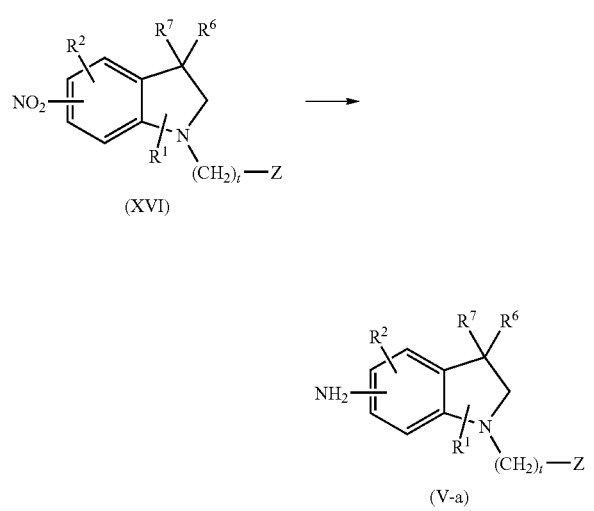

(V-a)

Intermediates of formula (X) can be prepared by reacting an intermediate of formula (XI) with an intermediate of formula (XII) in the presence of appropriate reagents such as N'-(ethylcarbonimidoyl)-N,N-dimethyl-1,3-propanediamine, monohydrochloride (EDC) and 1-hydroxy-1H-benzotriazole (HOBT). The reaction may be performed in the presence of a base such as triethylamine, in a suitable solvent, such as, a mixture of dichloromethane and tetrahydrofuran.

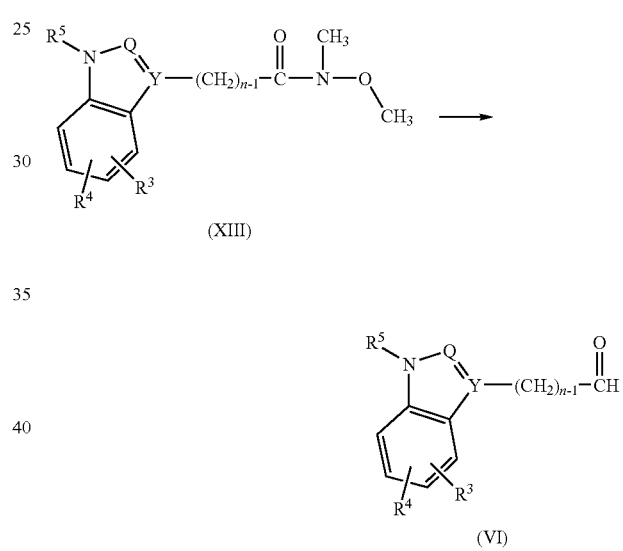

(XI)

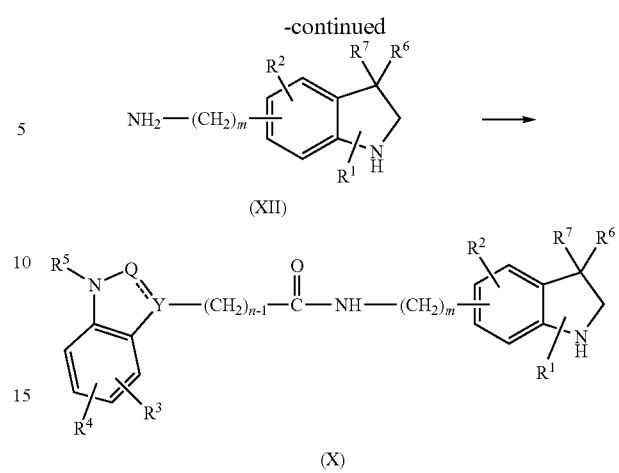

(XII)

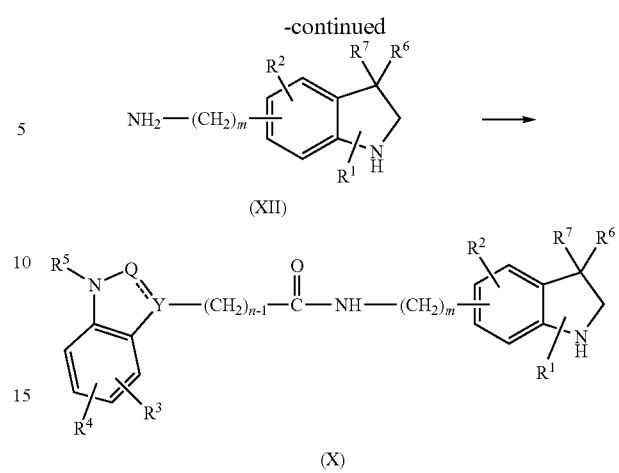

(X)

The intermediates of formula (VI) can be prepared by reacting intermediates of formula (XIII) with lithium aluminium hydride in a suitable solvent such as tetrahydrofuran.

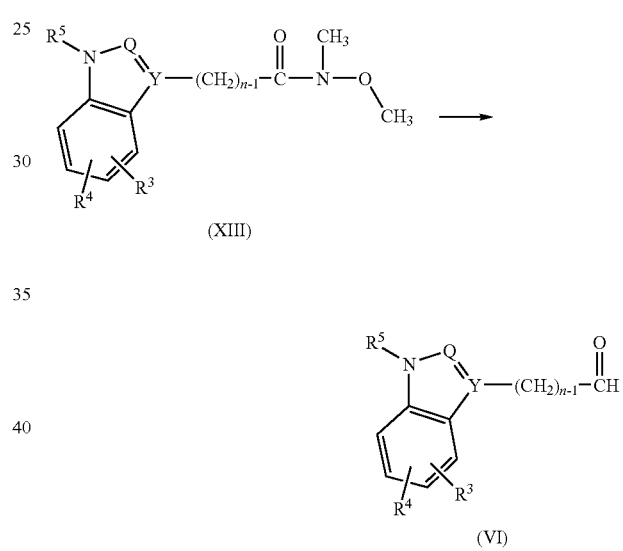

(XIII)

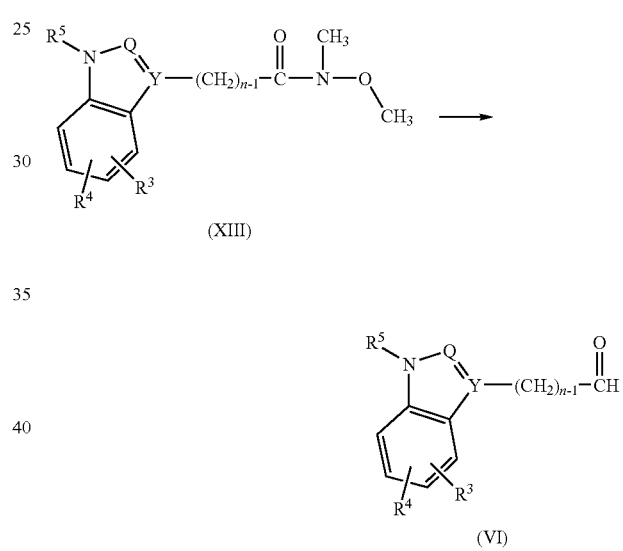

(VI)

The intermediates of formula (VIII) (idem for intermediates of formula (XVI)), wherein t is 0, herein referred to as intermediates of formula (VIII-a), can be prepared by reacting an intermediate of formula (IX) with an intermediate of formula (XIV), wherein L is an appropriate leaving group such as, for example, halo, e.g. fluoro, chloro, bromo or iodo, or $C_{1-6}$alkyloxy, e.g. methyloxy, in the presence of a hydrochloride solution in 2-propanol, in a reaction inert solvent such as N,N-dimethylformamide.

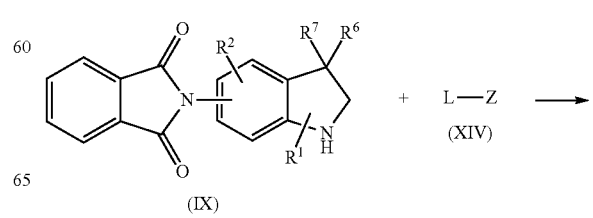

(IX)

-continued

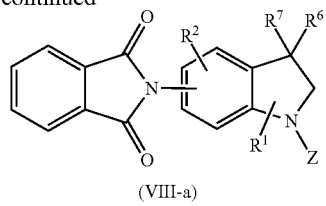

(VIII-a)

The intermediates of formula (IX), wherein $R^6$ and $R^7$ are both hydrogen, herein referred to as intermediates of formula (IX-a), can be prepared by converting an intermediate of formula (XV) in the presence of sodium cyanoborohydride. The reaction can be performed in a reaction-inert solvent such as, for example acetic acid,

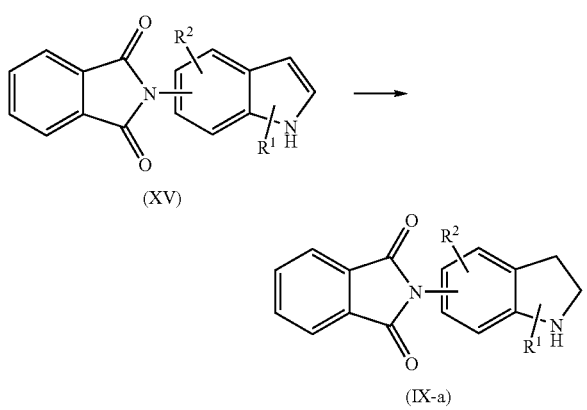

The compounds of formula (I) and some of the intermediates may have at least one stereogenic centre in their structure. Such stereogenic centre may be present in an R or an S configuration.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization, supercritical fluid chromatography or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

The compounds of formula (I), the pharmaceutically acceptable acid addition salts and stereoisomeric forms thereof have valuable pharmacological properties in that they inhibit the interaction between p53 and MDM2.

The term "MDM2" is used herein to mean a protein obtained as a result of expression of the mdm2 gene. Within the meaning of this term, MDM2 encompass all proteins encoded by mdm2, mutants thereof, alternative slice proteins thereof, and phosphorylated proteins thereof. Additionally, as used herein, the term "MDM2" includes MDM2 analogues, e.g. MDMX, also known as MDM4, and MDM2 homologues and analogues of other animals, e.g. the human homologue HDM2 or the human analogue HDMX.

The term "inhibiting the interaction" or "inhibitor of the interaction" is used herein to mean preventing or reducing the direct of indirect association of one or more molecules, peptides, proteins, enzymes or receptors; or preventing or reducing the normal activity of one or more molecules, peptides, proteins, enzymes, or receptors.

The term "inhibitor of the interaction of p53 with MDM2" or "p53-MDM2 inhibitor" is used herein to describe an agent which increases the expression of p53 in the assay described in C.1. This increase may be caused by, but is not limited to, one or more of the following mechanisms of action:
inhibiting the interaction between p53 and MDM2,
direct association with either the MDM2 or the p53 protein,
interactions with upstream or downstream targets, e.g. kinases, or enzyme activities involved in ubiquitination or SUMO modification,
sequestering or transportation of MDM2 and p53 into different cellular compartments,
modulation of proteins associating with MDM2, for example (but not limited to), p'73, E2F-1, Rb, p21wafl or cip1,
downregulating or interference with MDM2 expression and/or MDM2 activity, for example (but not limited to), impacting on its cellular localisation, post-translational modification, nuclear export or ubiquitin ligase activity,
direct or indirect stabilization of the p53 protein, e.g. by keeping it in its functional structural form, or by preventing misfolding,
enhancing p53 expression or expression of p53 family members, e.g. p63 and p73.
increasing p53 activity, for example by (but not limited to), enhancing its transcriptional activity and/or
increasing expression of genes and proteins of the p53-signalling pathway, for example (but not limited to) p21wafl, cip1, MIC-1 (GDF-15), PIG-3 and ATF-3.

Hence, the present invention discloses the compounds of formula (I) for use as a medicine.

Furthermore, the invention also concerns the use of a compound for the manufacture of a medicament for the treatment of a disorder mediated through a p53-MDM2 interaction, wherein said compound is a compound of formula (I)

The term "treating" or "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

With the term "a disorder mediated through a p53-MDM2 interaction" is meant any undesired or detrimental condition that results in or from the inhibition of the interaction between the MDM2 protein and p53 or other cellular proteins that induce apoptosis, induce cellular death, or regulate the cell cycle.

This invention also provides a method for treating a disorder mediated through a p53-MDM2 interaction by administering an effective amount of a compound of the present invention, to a subject, e.g. a mammal (and more particularly a human) in need of such treatment.

The compounds of the invention can have antiproliferative effects in tumour cells, even if such cells are devoid of functional p53. More in particular, the compounds of the invention can have antiproliferative effects in tumours with wild-type p53 and/or in tumours overexpressing MDM2.

Thus, this invention also provides a method for inhibiting tumour growth by administering an effective amount of a compound of the present invention, to a subject, e.g. a mammal (and more particularly a human) in need of such treatment.

Examples of tumours which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), oesophageal cancer, oral squamous carcinoma, tongue carcinoma, gastric carcinoma, nasopharyngeal cancer, hematopoietic tumours of lymphoid lineage (e.g. acute lymphocytic leukemia, B-cell lymphoma, Burkitt's lymphoma), non-Hodgkin's lymphoma, Hodgkin's disease, myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, brain tumors, gliomas, benign tumour of the skin (e.g. keratoacanthomas), breast carcinoma (e.g. advanced breast cancer), kidney carcinoma, ovary carcinoma, cervical carcinoma, endometrial carcinoma, bladder carcinoma, prostate cancer including the advanced disease, testicular cancers, osteosarcoma, head and neck cancer and epidermal carcinoma.

The compounds of the present invention can also be used for the treatment and prevention of inflammatory conditions.

Thus, this invention also provides a method for the treatment and prevention of inflammatory conditions by administering an effective amount of a compound of the present invention, to a subject, e.g. a mammal (and more particularly a human) in need of such treatment.

The compounds of the present invention can also be used for the treatment of autoimmune diseases and conditions. With the term "autoimmune diseases" is meant any disease in which an animal's immune system reacts adversely to a self-antigen. With the term "self-antigen" is meant any antigen that is normally found in the animal's body. Representative autoimmune diseases include but are not limited to: Hashimoto's thyroiditis, Grave's disease, multiple sclerosis, pernicious anemia, Addison's disease, insulin-dependent diabetes mellitus, rheumatoid arthritis, systemic lupus erythematosus (SLE or lupus), dermatomyositis, Crohn's disease, Wegener's granulomatosis, Anti Glomerular Basement Membrane Disease, Antiphospholipid Syndrome, Dermatitis Herpetiformis, Allergic Encephalomyelitis, Glomerulonephritis, Membranous Glomerulonephritis, Goodpasture Syndrome, Lambert-Eaton, Myasthenic Syndrome, Myasthenia Gravis, Bullous Pemphigoid, Polyendocrinopathies, Reiter's Disease, and Stiff-Man Syndrome.

Thus, this invention also provides a method for the treatment of autoimmune diseases and conditions and the treatment of diseases associated with conformational unstable or misfolded proteins by administering an effective amount of a compound of the present invention, to a subject, e.g. a mammal (and more particularly a human) in need of such treatment.

The compounds of the present invention can also be useful for the treatment of diseases associated with conformational unstable or misfolded proteins. Examples of diseases associated with conformational unstable or misfolded proteins include but are not limited to: cystic fibrosis (CFTR), Marfan syndrom (fibrillin), Amyotrophic lateral sclerosis (superoxide dismutase), scurvy (collagen), maple syrup urine disease (alpha-ketoacid dehydrogenase complex), osteogenesis imperfecta (type1 procollagen pro-alpha), Creutzfeldt-Jakob disease (prion), Alzheimer's disease (beta-amyloid), familial amyloidosis (lysozyme), cataracts (crystallins), familial hypercholesterolemia (LDL receptor), α I-antitrypsin deficiency, Tay-Sachs disease (beta-hexosaminidase), retinitis pigmentosa (rhodopsin), and leprechaunism (insulin receptor).

Thus, this invention also provides a method for the treatment of diseases associated with conformational unstable or misfolded proteins by administering an effective amount of a compound of the present invention, to a subject, e.g. a mammal (and more particularly a human) in need of such treatment.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to inhibit the interaction between MDM2 and p53 or other cellular proteins that induce apoptosis, induce cellular death, or regulate the cell cycle.

The oncogenic potential of MDM2 is not only determined by its ability to suppress p53, but also by its ability to regulate other tumour suppressor proteins, e.g. the retinoblastoma protein pRb and the closely associated E2F1 transcription factor.

Thus, the compound of the invention is administered in an amount sufficient to modulate the interaction between MDM2 and the E2F transcription factors.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

As another aspect of the present invention, a combination of a p53-MDM2 inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents include bur are not limited to:
  platinum coordination compounds for example cisplatin, carboplatin or oxalyplatin;
  taxane compounds for example paclitaxel or docetaxel;
  topoisomerase I inhibitors such as camptothecin compounds for example irinotecan or topotecan;
  topoisomerase II inhibitors such as anti-tumour epipodophyllotoxins or podophyllotoxin derivatives for example etoposide or teniposide;
  anti-tumour vinca alkaloids for example vinblastine, vincristine or vinorelbine;
  anti-tumour nucleoside derivatives for example 5-fluorouracil, leucovorin, gemcitabine or capecitabine;
  alkylating agents such as nitrogen mustard or nitrosourea for example cyclophosphamide, chlorambucil, carmustine, thiotepa, mephalan or lomustine;
  anti-tumour anthracycline derivatives for example daunorubicin, doxorubicin, doxil, idarubicin or mitoxantrone;
  molecules that target the IGF-1 receptor for example picropodophilin;
  tetracarcin derivatives for example tetrocarcin A;
  glucocorticoïden for example prednisone;
  antibodies for example trastuzumab (HER2 antibody), rituximab (CD20 antibody), gemtuzamab, cetuximab, pertuzumab or bevacizumab;
  estrogen receptor antagonists or selective estrogen receptor modulators for example tamoxifen, fulvestrant, toremifene, droloxifene, faslodex or raloxifene;
  aromatase inhibitors such as exemestane, anastrozole, letrazole and vorozole;
  differentiating agents such as retinoids, vitamin D or retinoic acid and retinoic acid metabolism blocking agents (RAMBA) for example accutane;
  DNA methyl transferase inhibitors for example azacytidine or decitabine;
  antifolates for example premetrexed disodium;
  antibiotics for example antinomycin D, bleomycin, mitomycin C, dactinomycin, caminomycin or daunomycin;
  antimetabolites for example chlofarabine, aminopterin, cytosine arabinoside or methotrexate;
  apoptosis inducing agents and antiangiogenic agents such as Bcl-2 inhibitors for example YC 137, BH 312, ABT 737, gossypol, HA 14-1, TW 37 or decanoic acid;
  tubuline-binding agents for example combrestatin, colchicines or nocodazole;
  kinase inhibitors for example flavoperidol, imatinib mesylate, erlotinib or gefitinib;
  farnesyltransferase inhibitors for example tipifarnib;
  histone deacetylase (HDAC) inhibitors for example sodium butyrate, suberoylanilide hydroxamide acid (SAHA), depsipeptide (FR 901228), NVP-LAQ824, R306465, JNJ-26481585 or trichostatin A;
  Inhibitors of the ubiquitin-proteasome pathway for example PS-341, MLN 0.41 or bortezomib;
  Yondelis;
  Telomerase inhibitors for example telomestatin;
  Matrix metalloproteinase inhibitors for example batimastat, marimastat, prinostat or metastat.

As stated above, the compounds of the present invention also have therapeutic applications in sensitising tumour cells for chemotherapy and radiotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same. Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other disease.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonist, for example vcrapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the other medicinal agent and the p53-MDM inhibitor may be formulated into various pharmaceutical forms for administration purposes. The components may be formulated separately in individual pharmaceutical compositions or in a unitary pharmaceutical composition containing both components.

The present, invention therefore also relates to a pharmaceutical composition comprising the other medicinal agent and the p53-MDM inhibitor together with one or more pharmaceutical carriers.

The present invention further relates to the use of a combination according to the invention in the manufacture of a pharmaceutical composition for inhibiting the growth of tumour cells.

The present invention further relates to a product containing as first active ingredient a p53-MDM2 inhibitor according to the invention and as second active ingredient an anticancer agent, as a combined preparation for simultaneous, separate or sequential use in the treatment of patients suffering from cancer.

The other medicinal agent and p53-MDM2 inhibitor may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and p53-MDM2 inhibitor being administered, their route of administration, the particular tumour being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

These dosages may be administered for example once, twice or more per course of treatment, which may be repeated for example every 7, 14, 21 or 28 days.

The compounds of formula (I), the pharmaceutically acceptable acid addition salts and stereoisomeric forms thereof can have valuable diagnostic properties in that they can be used for detecting or identifying an p53-MDM2 interaction in a biological sample comprising detecting or measuring the formation of a complex between a labelled compound and/or p53 and/or MDM2 and or other molecules, peptides, proteins, enzymes or receptors.

The detecting or identifying methods can use compounds that are labelled with labelling agents such as radioisotopes, enzymes, fluorescent substances, luminous substances, etc.

Examples of the radioisotopes include $^{125}$I, $^{131}$I, $^{3}$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

The following examples illustrate the present invention.

EXPERIMENTAL PART

Hereinafter, "DMF" is defined as N,N-dimethylformamide, "DCM" is defined as dichloromethane, "EtOAc" is defined as ethyl acetate, "EtOH" is defined as ethanol, "MeOH" is defined as methanol and "THF" is defined as tetrahydrofuran.

Melting Points

For a number of compounds, melting points were obtained with a Kofler hot bench, consisting of a heated plate with linear temperature gradient, a sliding pointer and a temperature scale in degrees Celsius.

LCMS

Method A

The HPLC gradient was supplied by an Alliance HT 2795 (Waters) system comprising a quaternary pump with degasser, an autosampler and a diode-array detector (DAD). Flow from the column was split to a MS detector. The MS detector was configured with an electrospray ionization source. The capillary needle voltage was 3 kV and the source temperature was maintained at 100° C. on the LCT (Time of Flight-Z-spray mass spectrometer from Waters. Nitrogen was used as the nebulizer gas. Data acquisition was performed with a Waters-Micromass MassLynx-Openlynx data system. Reversed phase HPLC was carried out on n Xterra-RP C18 column (5 μm, 3.9×150 mm) with a flow rate of 1.0 ml/min at a temperature of 30° C. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 μl was used. Cone voltage was 20 V for positive ionization mode. Mass spectra were acquired by scanning from 100 to 900 in 0.8 seconds using an interscan delay of 0.08 seconds.

Method B

The LC gradient was supplied by an Acquity UPLC (Waters) system comprising a binary pump, a sample organizer, a column heater (set at 55° C.) and diode-array detector (DAD). Flow from the column was split to a MS detector. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

Reversed phase UPLC was carried out on a bridged ethylsiloxane/silica (BEH) C18 column (1.7 μm, 2.1×50 mm) with a flow rate of 0.8 ml/min. Two mobile phases (mobile phase A: 0.1% formic acid in H$_2$O/methanol 95/5; mobile phase B: methanol) were used to run a gradient condition from 95% A to 5% A, 95% B in 1.3 minutes and hold for 0.2 minutes. An injection volume of 0.5 μl was used.

Cone voltage was 10 V for positive ionization mode and 20 V for negative ionization mode.

A. Preparation of the Intermediate Compounds

Example A1 a) Preparation of Intermediate 1

To a solution of 5-nitroindoline (10.0 g, 0.061 mol) and 4-chloropyridine hydrochloride (11.0 g, 0.073 mol) in DMF (60 ml), under argon, at 0° C., was added portionwise potassium tert-butoxide (17.0 g, 0.15 mol). The mixture was heated up to 100° C. for 16 hours. The mixture was poured into ice and extracted twice with EtOAc. The organic layer separated, dried (MgSO$_4$), filtered and the solvent was evaporated. The residue was purified twice by column chromatography over silica gel (40-63 μm) (eluent: cyclohexane/EtOAc/MeOH 50/50/0 to 0/80/20). The pure fractions were collected and the solvent was evaporated, yielding 2.49 g (17%) of intermediate 1 as a brown-orange solid.

$^1$H NMR (300 MHz, DMSO-d$_6$) δ 8.47 (dd, 2H, J=6.4, J=1.6), 8.06 (m, 2H), 7.41 (d, 1H, J=9.6), 7.28 (dd, 2H, J=6.4, J=1.6), 4.16 (t, 2H, J=8.6), 3.22 (t, 2H, J=8.6).
MS (ES+) m/z 242 (M+1).

b) Preparation of Intermediate 2

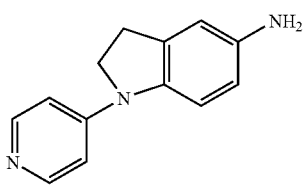

A mixture of intermediate 1 (2.4 g, 0.010 mol) and Raney Nickel (5 ml, 50% slurry in water) in EtOH (45 ml) and THF (45 ml) was stirred at room temperature under 30 psi of hydrogen for 3 hours. After filtration through a celite pad, the solvent was evaporated to give 2.01 g (96%) of intermediate 2 as a brown solid.

$^1$H NMR (300 MHz, CDCl$_3$) δ 8.32 (dd, 2H, J=6.4, J=1.5), 7.15 (d, 1H, J=8.5), 6.92 (dd, 2H, J=6.4, J=1.5), 6.63 (d, 1H, J=2.2), 6.50 (dd, 1H, J=8.3, J=2.4), 3.92 (t, 2H, J=8.3), 3.44 (brs, 2H), 3.08 (t, 2H, J=8.3).

c) Preparation of Intermediate 3

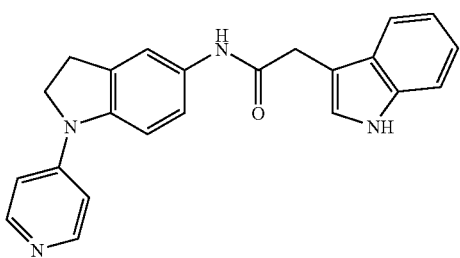

To a solution of intermediate 2 (1.9 g, 0.0089 mol) in DCM (20 ml) and THF (20 ml), under argon, were added successively indole-3-acetic acid (2.0 g, 0.012 mol), 1-hydroxybenzotriazole hydrate (1.6 g, 0.012 mol) and 1-(3-dimethylaminopropyl)-3-ethylcarbodiimide hydrochloride (2.2 g, 0.012 mol). The reaction mixture was stirred at room temperature for 40 hours. To complete the reaction, indole-3-acetic acid (1.6 g, 0.0089 mol) and 1-(3-dimethylaminopropyl)-3-ethylcarbodiimide hydrochloride (1.7 g, 0.0089 mol) were added and the mixture was stirred at room temperature for 16 more hours. The solvents were evaporated and the residue was purified by column chromatography over silica gel (40-63 μm) (eluent: DCM/MeOH/NH$_4$OH 95/5/0.1 to 80/20/0.1). The collected fractions were evaporated, the resulting solid was washed with MeOH and dried, yielding 1.95 g (60%) of intermediate 3.

$^1$H NMR (300 MHz, DMSO-d$_6$) δ 10.93 (brs, 1H), 10.08 (brs, 1H), 8.31 (d, 2H, J=6.3), 7.88 (d, 1H, J=8.1), 7.58 (m, 2H), 7.34 (m, 2H), 7.26 (d, 1H, J=2.1), 7.17 (d, 2H, J=6.6), 7.07 (t, 1H, J=6.9), 6.98 (t, 1H, J=7.4), 3.99 (t, 2H, J=8.3), 3.71 (s, 2H), 3.12 (t, 2H, J=8.2).
MS (ES+) m/z 369 (M+1).

Example A2 a) Preparation of Intermediate 4

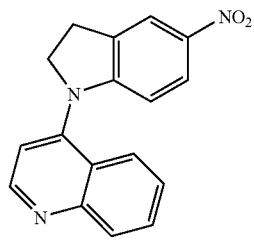

To a solution of 5-nitroindoline (5.0 g, 0.030 mol) and 4-chloroquinoline (6.0 g, 0.037 mol) in DMF (30 ml), under argon, was added portionwise potassium tert-butoxide (8.4 g, 0.075 mol). The mixture was stirred at 100° C. for 16 hours then at room temperature for 70 hours. The mixture was poured into ice and extracted 3 times with EtOAc. The organic layer was separated, washed with brine, dried (MgSO$_4$), filtered and the solvent was evaporated. The residue was purified by column chromatography over silica gel (40-63 μm) (eluent: EtOAc/cyclohexane 50/50 to 100/0). The pure fractions were collected and the solvent was evaporated, yielding 2.26 g (26%) of intermediate 4 as an orange solid.

$^1$H NMR (300 MHz, CDCl$_3$) δ 8.93 (d, 1H, J=4.9), 8.11 (m, 2H), 7.92 (dd, 1H, J=8.9, J=2.5), 7.85 (d, 1H, J=7.7), 7.82 (dt, 1H, J=7.0, J=1.4), 7.60 (dt, 1H, J=6.8, J=1.2), 7.54 (d, 1H, J=4.9), 6.26 (d, 1H, J=8.9), 4.30 (t, 2H, J=8.4), 3.35 (t, 2H, J=8.2).
MS (ES+) m/z 292 (M+1).

b) Preparation of Intermediate 5

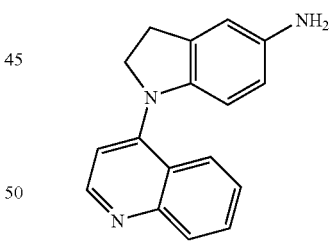

A mixture of intermediate 4 (2.0 g, 0.0069 mol) and Raney Nickel (3 ml, 50% slurry in water) in EtOH (30 ml) and THF (30 ml) was stirred at room temperature under 30 psi of hydrogen for 4.5 hours. After filtration through a celite pad, the solvent was evaporated, yielding 1.81 g (100%) of intermediate 5 as an orange solid.

$^1$H NMR (300 MHz, CDCl$_3$) δ 8.71 (d, 1H, T=5.1), 8.07 (d, 1H, J=8.5), 8.01 (d, 1H, J=8.5), 7.67 (t, 1H, J=7.0), 7.41 (t, 1H, J=7.1), 7.09 (d, 1H, J=5.1), 6.67 (s, 1H), 6.49 (d, 1H, J=8.3), 6.38 (dd, 1H, J=8.3, J=1.9), 4.04 (t, 2H, J=7.9), 3.39 (brs, 2H), 3.12 (t, 2H, J=7.8).
MS (ES+) m/z 262 (M+1).

c) Preparation of Intermediate 6

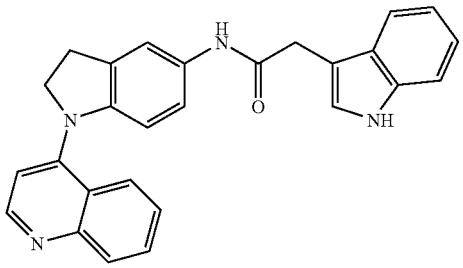

To a solution of intermediate 5 (1.7 g, 0.0064 mol) in DCM (15 ml) and THF (15 ml), under argon, were added successively indole-3-acetic acid (1.5 g, 0.0084 mol), 1-hydroxybenzotriazole hydrate (1.1 g, 0.0084 mol) and 1-(3-dimethylaminopropyl)-3-ethylcarbodiimide hydrochloride (1.6 g, 0.0084 mol). The mixture was stirred at room temperature for 16 hours. The solvents were evaporated and the residue was purified by column chromatography over silica gel (40-63 µm) (eluent: DCM/MeOH/NH$_4$OH 90/10/0.1). The pure fractions were collected and the solvent was evaporated, yielding 1.15 g (43%) of intermediate 6 as a brown foam.

$^1$H NMR (300 MHz, CDCl$_3$) δ 8.74 (d, 1H, J=5.1), 8.61 (brs, 1H), 8.09 (d, 1H, J=8.1), 7.91 (d, 1H, J=8.4), 7.70-7.62 (m, 2H), 7.41 (m, 4H), 7.22 (m, 3H), 7.09 (d, 1H, J=5.1), 6.74 (dd, 1H, J=8.4, J=1.8), 6.38 (d, 1H, J=8.4), 4.04 (t, 2H, J=8.0), 3.89 (s, 2H), 3.15 (t, 2H, J=7.9).

MS (ES+) m/z 419 (M+1).

Example A3

Preparation of Intermediate 7

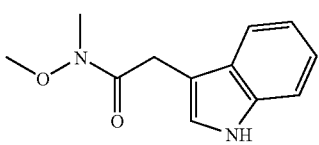

A mixture of indole-3-acetic acid (2.0 g, 0.013 mol) and 1,1-carbonyldiimidazole (2.1 g, 0.013 mol, added portionwise) in DCM (28 ml) was stirred under argon at room temperature for 2 hours. N,O-dimethylhydroxylamine hydrochloride (1.3 g, 0.013 mol) was added, the mixture was stirred at room temperature for 16 hours, and then poured out into ice and water. The pH was adjusted to 10 with a 4N solution of sodium hydroxide, and the aqueous layer was extracted twice with EtOAc. The organic layer was separated, washed with a 3N hydrochloride solution, dried (MgSO$_4$), filtered, and the solvent was evaporated, yielding 2.37 g (89%) of intermediate 7 as a pink solid.

$^1$H NMR (300 MHz, CDCl$_3$) δ 8.09 (brs, 1H), 7.66 (d, 1H, J=7.5), 7.36 (d, 1H, J=7.5), 7.22-7.10 (m, 3H), 3.92 (s, 2H), 3.66 (s, 3H), 3.23 (s, 3H).

Example A4 a) Preparation of Intermediate 8

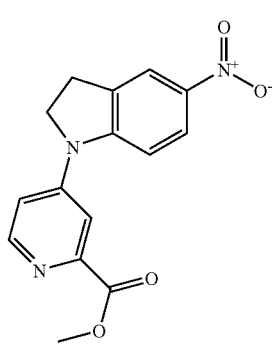

A mixture of 5-nitroindoline (4.0 g, 0.024 mol) and 4-chloro-2-pyridinecarboxylic acid, methyl ester (5.0 g, 0.029 mol) in acetic acid (24 ml), was heated up to 120° C. for 25 minutes in a Biotage Initiator microwave apparatus. The reaction was quenched with ice, the pH was adjusted to pH 9 by addition of a saturated solution of potassium carbonate. The mixture was extracted 3 times with DCM. The organic layer was separated, dried (MgSO$_4$), filtered and the solvent was evaporated. The residue was purified by column chromatography over silica gel (40-63 µm) (eluent: DCM/MeOH 100/0 to 90/10). The pure fractions were collected and the solvent was evaporated, yielding 1.37 g (19%) of intermediate 8 as a yellow solid.

$^1$H NMR (300 MHz, CDCl$_3$) δ 8.65 (d, 1H, J=5.6), 8.16 (dd, 1H, J=8.9, J=2.1), 8.11 (s, 1H), 7.98 (d, 1H, J=2.5), 7.35 (d, 1H, J=8.9), 7.30 (dd, 1H, J=5.7, J=2.5), 4.23 (t, 2H, J=8.5), 4.05 (s, 3H), 3.32 (t, 2H, J=8.4).

MS (ES+) m/z 300 (M+1).

b) Preparation of Intermediate 9

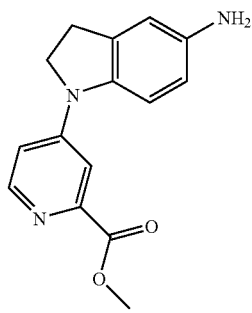

A mixture of intermediate 8 (1.2 g, 0.0045 mol) and Raney Nickel (4 ml, 50% slurry in water) in MeOH (20 ml) and THF (20 ml) was stirred at room temperature under 1 atmosphere of hydrogen for 20 hours. After filtration through a celite pad, the solvent was evaporated, yielding 1.06 g (88%) of intermediate 9 as an orange solid.

$^1$H NMR (300 MHz, CDCl$_3$) δ 8.40 (d, 1H, J=5.8), 7.77 (d, 1H, J=2.5), 7.18 (d, 1H, J=8.4), 7.05 (dd, 1H, J=5.8, J=2.6), 6.62 (d, 1H, J=2.2), 6.52 (dd, 1H, J=8.4, J=2.4), 4.00 (m, 5H), 3.09 (t, 2H, J=8.3).

MS (ES+) m/z 270 (M+1).

Example A5 a) Preparation of Intermediate 10

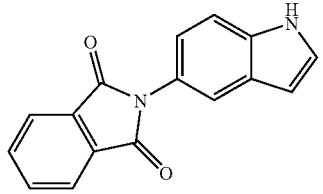

A mixture of 5-aminoindole (1.1 g, 0.0086 mol) and phthalic anhydride (2.6 g, 0.017 mol) in DMF (20 ml) was stirred at 100° C. for 5 hours, then at room temperature for 64 hours. The reaction mixture was diluted in EtOAc, washed twice with a saturated solution of ammonium chloride, dried (MgSO$_4$), filtered, and the solvent was evaporated. The resulting oil was taken up in acetic acid (15 ml) and stirred at room temperature for 20 minutes, then heated up to 80° C. for 1.5 hour. Ice was added and the pH was adjusted to pH 4 with a saturated solution of sodium carbonate. The mixture was extracted twice with EtOAc. The organic layer was separated, dried (MgSO$_4$), filtered, and the solvent was evaporated. The residue was purified by column chromatography over silica gel (40-63 μm) (eluent: EtOAc/cyclohexane 40/60). The pure fractions were collected and the solvent was evaporated, yielding 2.06 g (91%) of intermediate 10.

$^1$H NMR (300 MHz, CDCl$_3$) δ 8.32 (brs, 1H), 7.97 (m, 2H), 7.79 (m, 2H), 7.66 (d, 1H, J=2.0), 7.49 (d, 1H, J=8.6), 7.27 (dd, 1H, J=5.7, J=2.8), 7.17 (dd, 1H, J=8.6, J=2.0), 6.61 (t, 1H, J=1.1).

MS (ES+) m/z 263 (M+1).

b) Preparation of intermediate 11

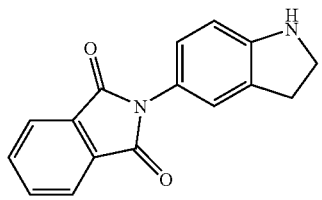

A mixture of intermediate 10 (2.1 g, 0.0079 mol) and sodium cyanoborohydride (987 mg, 0.016 mol) in acetic acid (30 ml) was stirred at room temperature for 18 hours. Ice was added and the pH was adjusted to 6 with a saturated solution of sodium carbonate. The mixture was extracted twice with EtOAc. The organic layer was separated, washed with brine, dried (MgSO$_4$), filtered, and the solvent was evaporated. The residue was purified by column chromatography over silica gel (40-63 μm) (eluent: EtOAc/cyclohexane 30/70 to 70/30). The pure fractions were collected and the solvent was evaporated, yielding 726 mg (35%) of intermediate 11 as a yellow solid.

$^1$H NMR (300 MHz, CDCl$_3$) δ 7.93 (m, 2H), 7.77 (m, 2H), 7.09 (s, 1H), 7.00 (d, 1H, J=8.2), 6.70 (d, 1H, J=8.2), 3.62 (t, 2H, J=8.4), 3.09 (t, 2H, J=8.4).

MS (ES+) m/z 265 (M+1).

c) Preparation of Intermediate 12

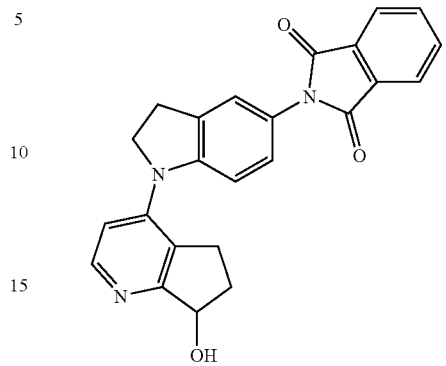

A mixture of intermediate 11 (570 mg, 0.0022 mol), 4-bromo-6,7-dihydro-5H-[1]pyridin-7-ol (554 mg, 0.0026 mol) and a 5N hydrochloride solution in 2-propanol (0.57 ml, 0.0029 mol) in DMF (11 ml) was heated up to 120° C. for 1 hour in a Biotage Initiator microwave apparatus. The reaction was quenched with a saturated solution of sodium hydrogen carbonate and extracted 3 times with DCM. The solvents were evaporated. The residue was purified by column chromatography over silica gel (40-63 μm) (eluent: EtOAc/ MeOH 100/0 to 80/20 then DCM/MeOH 95/5 to 90/10). The pure fractions were collected and the solvent was evaporated, yielding 651 mg (76%) of intermediate 12 as a yellow solid.

$^1$H NMR (300 MHz, CDCl$_3$) δ 8.30 (d, 1H, J=5.6), 7.95 (m, 2H), 7.79 (m, 2H), 7.23-7.12 (m, 3H), 6.94 (d, 1H, J=8.4), 5.24 (t, 1H, J=7.0), 4.18 (m, 1H), 4.08 (m, 1H), 3.25 (m, 2H), 3.00 (m, 1H), 2.85 (m, 1H), 2.57 (m, 1H), 2.06 (m, 1H).

MS (ES+) m/z 398 (M+1).

d) Preparation of Intermediate 13

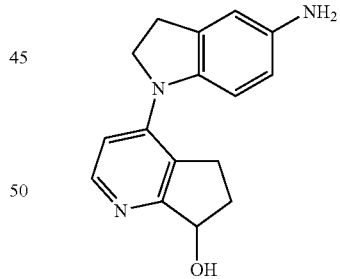

At room temperature, hydrazine hydrate (137 μl, 0.0028 mol) was added to a suspension of intermediate 12 (557 mg, 0.0014 mol) in MeOH (5.5 ml) and the resulting mixture was heated up to 70° C. for 40 minutes. The reaction was quenched with water and extracted 4 times with EtOAc. The organic layer was separated, dried (MgSO$_4$), filtered, and the solvent was evaporated, yielding 392 mg (100%) of intermediate 13 as a brown-orange solid.

$^1$H NMR (300 MHz, CDCl$_3$) δ 8.18 (d, 1H, J=5.8), 7.07 (d, 1H, J=5.8), 6.49 (d, 1H, J=8.3), 6.63 (d, 1H, J=2.1), 6.48 (dd, 1H, J=8.3, J=2.4), 5.21 (m, 1H), 4.19 (brs, 2H), 4.03 (m, 3H), 3.05 (m, 3H), 2.84 (m, 1H), 2.50 (m, 1H), 2.03 (m, 1H).

Example A6 a) Preparation of Intermediate 14

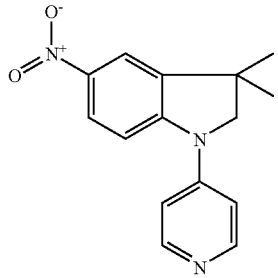

A mixture of 2,3-dihydro-3,3-dimethyl-5-nitro-1H-indole (0.003 mol) and 4-bromo-pyridine (0.003 mol) in 1-butanol (5 ml) was heated in a sealed tube in a microwave oven at 140° C. for 30 minutes, then taken up in a solution of 10% potassium carbonate and extracted with EtOAc. The organic layer was washed with water, then with NaCl and brine, dried (MgSO$_4$), filtered, and the solvent was evaporated. The residue (0.8 g) was purified by column chromatography over silica gel (20-45 µm) (eluent: DCM/MeOH 100/0 to 98/2). The pure fractions were collected and the solvent was evaporated. The residue (0.45 g, 64%) was crystallized from acetonitrile. The precipitate was filtered off and dried, yielding 0.216 g (31%) of intermediate 14, melting point 217° C. (Kofler).

$^1$H NMR (DMSO-d$_6$) δ1.4 (6H,s), 3.92 (2H,s), 7.3 (2H,m), 7.45 (1H,m), 8.10 (2H,m), 8.47(2H,m)

LCMS (ES+) m/z 270 (M+1), R$_t$=0.77, Method B b) Preparation of Intermediate 15

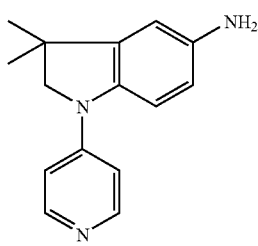

A mixture of intermediate 14, (0.003 mol) and Raney Nickel (0.9 g) in MeOH (20 ml) was hydrogenated at room temperature for 1 hour under a 3 bar pressure, then filtered over celite. Celite was washed with MeOH. The filtrate was evaporated, yielding 0.8 g (100%) of intermediate 15.

c) Preparation of Intermediate 16

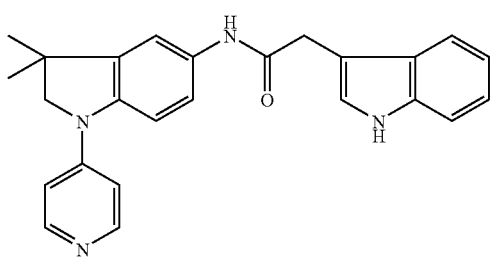

Bromotris(pyrrolidino)phosphonium hexafluorophosphate (0.004 mol) was added portionwise at room temperature to a solution of intermediate 15 (0.003 mol), 1H-indole-3-acetic acid (0.004 mol), 1-hydroxybenzotriazole (0.04 mol) and diisopropyl ether (0.005 mol) in DCM (15 ml). The mixture was stirred at room temperature overnight. The organic layer was washed with a solution of 10% potassium carbonate, dried (MgSO$_4$), filtered and the solvent was evaporated. The residue (3.2 g) was purified by column chromatography over silica gel (15-40 µm) (eluent: DCM/MeOH/NH$_4$OH 95/5/0.2). The pure fractions were collected and the solvent was evaporated. The residue (0.7 g, 52%) was crystallized from acetonitrile. The precipitate was filtered off and dried, yielding 0.55 g (41%) of intermediate 16, melting point 158° C. (Kofler).

$^1$H NMR (DMSO-d$_6$), δ1.28(6H, ), 3.7(2H,s), 3.73(2H,s), 6.99(1H,t, J=7.7Hz), 7.07-7.11 (3H,m), 2.25(1H,d,J=3.6Hz), 7.30-7.39(3H,m), 7.55(1H,br,d, J=3.6 Hz), 7.62(1H,d, J=7.7Hz), 8.3(2H,d,J=7.7Hz), 10.03(1H,br,s), 10.92(1H,br, s)

LCMS (ES+) m/z 397 (M+1), R$_t$=8.43, method A

B. Preparation of the Final Compounds

Example B1

Preparation of Compound 1

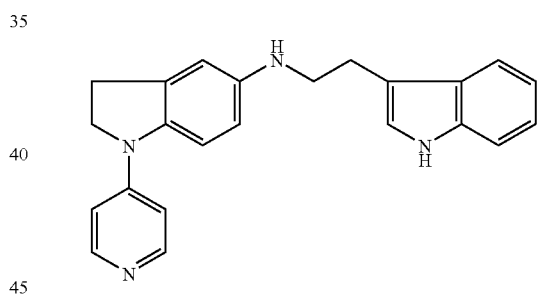

Lithium aluminum hydride (423 mg, 0.0011 mol) was added portionwise to a suspension of intermediate 3 (1.0 g, 0.0027 mol) in THF (60 ml) under argon. The mixture was stirred at room temperature for 24 hours, quenched with ice and a diluted Rochelle salt solution, and extracted 3 times with DCM. The organic layer was separated, dried (MgSO$_4$), filtered, and the solvent was evaporated. The residue was purified by column chromatography over silica gel (40-63 µm) (eluent: DCM/MeOH/NH$_4$OH 95/5/0.1). The pure fractions were collected and the solvent was evaporated, yielding 170 mg (18%) of compound 1 as a yellow foam.

$^1$H NMR (300 MHz, CDCl$_3$) δ 8.36 (brs, 1H), 8.32 (d, 2H, J=6.6), 7.63 (d, 1H, J=7.8), 7.39 (d, 1H, J=7.5), 7.24-7.11 (m, 3H), 7.07 (d, 1H, J=1.8), 6.93 (d, 2H, J=6.6), 6.58 (s, 1H), 6.45 (dd, 1H, J=8.4, J=2.1), 3.93 (t, 2H, J=8.2), 3.62 (brs, 1H), 3.46 (t, 2H, J=7.5), 3.09 (m, 4H).

LCMS (ES+) m/z 355 (M+1), R$_t$=8.30, method A

Example B2

Preparation of Compound 2

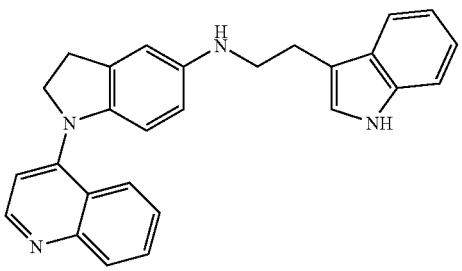

Under argon, at room temperature, lithium aluminum hydride (391 mg, 0.010 mol) was added portionwise to a solution of intermediate 6 (1.1 g, 0.0026 mol) in THF (55 ml). The mixture was stirred at room temperature for 18 hours. The reaction was quenched at 0° C. with MeOH. Ice and dilute Rochelle salt solution were added, and the mixture was extracted 3 times with DCM. The organic layer was separated, washed with brine, dried (MgSO$_4$), filtered, and the solvent was evaporated. The residue was purified by column chromatography over silica gel (40-63 μm) (eluent: DCM/MeOH/NH$_4$OH 97/3/0.5). The pure fractions were collected and the solvent was evaporated, yielding 121 mg (12%) of compound 2 as an orange foam.

$^1$H NMR (300 MHz, CDCl$_3$) δ 8.70 (d, 1H, J=5.1), 8.18 (brs, 1H), 8.07 (d, 1H, J=8.7), 8.03 (d, 1H, J=8.7), 7.66 (m, 2H), 7.41 (m, 2H), 7.22 (t, 1H, J=7.7), 7.12 (m, 3H), 6.63 (s, 1H), 6.56 (d, 1H, J=8.4), 6.34 (dd, 1H, J=8.4, J=2.1), 4.06 (t, 2H, J=7.8), 3.46 (t, 2H, J=6.8), 3.12 (m, 4H).

MS (ES+) m/z 405 (M+1).

Example B3

Preparation of Compound 3

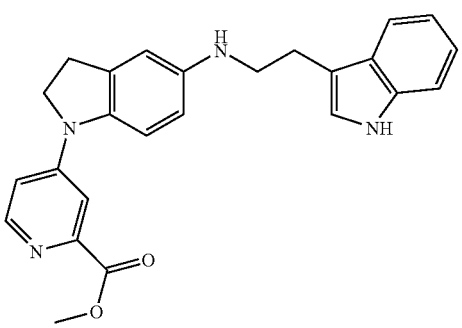

At 0° C. under argon, lithium aluminum hydride (14 mg, 0.00036 mol) was added to a solution of intermediate 7 (74 mg, 0.00036 mol) in THF (1 ml). The mixture was stirred at 0° C. for 1 hour, quenched with a 5% solution of potassium hydrogen sulfate, and extracted twice with EtOAc. The organic layer was separated, washed with brine, dried (MgSO$_4$), filtered, and the solvent was evaporated, to give the indole-3-yl acetaldehyde as an orange oil.

A mixture of intermediate 9 (200 mg, 0.00074 mol) and sodium cyanoborohydride (64 mg, 0.0010 mol) in MeOH (2.3 ml) and acetic acid (2 drops) was added dropwise to a solution of the previous aldehyde (236 mg, 0.0015 mol) in MeOH (2 ml). The reaction mixture was stirred at room temperature for 16 hours. The reaction was quenched with water, made alkaline with a saturated solution of sodium hydrogen carbonate and extracted 3 times with EtOAc. The organic layer was separated, washed with brine, dried (MgSO$_4$), filtered, and the solvent was evaporated. The residue was purified by column chromatography over silica gel (40-63 μm) (eluent: EtOAc/MeOH 100/0 to 90/10). The pure fractions were collected and the solvent was evaporated, yielding 190 mg (44%) of compound 3 as an orange foam.

$^1$H NMR (300 MHz, CDCl$_3$) δ 8.42 (d, 1H, J=5.7), 8.08 (brs, 1H), 7.79 (d, 1H, J=2.4), 7.63 (d, 1H, J=7.8), 7.40 (d, 1H, J=8.1), 7.25-7.07 (m, 5H), 6.59 (s, 1H), 6.48 (dd, 1H, J=8.7, J=2.1), 4.00 (m, 5H), 3.48 (t, 2H, J=6.8), 3.12 (m, 4H).

MS (ES+) m/z 413 (M+1).

Example B4

Preparation of Compound 4

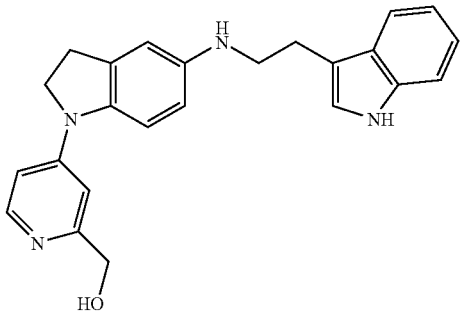

Sodium borohydride (92 mg, 0.0024 mol) was slowly added to a solution of compound 3 (100 mg, 0.00024 mol) in MeOH (3 ml). The mixture was stirred at room temperature for 1 hour then at 80° C. for 4 hours and again at room temperature for 85 hours. The reaction was quenched with water and the mixture was extracted with EtOAc. The organic layer was separated, washed with brine, dried (MgSO$_4$), filtered, and the solvent was evaporated. The residue was purified by column chromatography over silica gel (40-63 μm) (eluent: DCM/MeOH 90/10 to 85/15). The pure fractions were collected and the solvent was evaporated, yielding 50 mg (54%) of compound 4 as a yellow foam.

$^1$H NMR (300 MHz, DMSO-d$_6$) δ 10.83 (brs, 1H), 8.14 (d, 1H, J=5.7), 7.54 (d, 1H, J=7.8), 7.35 (d, 1H, J=7.8), 7.22 (m, 2H), 7.14 (d, 1H, J=2.1), 7.70 (dt, 1H, J=7.6, J=1.2), 6.98 (dt, 1H, J=7.5, J=0.9), 6.86 (dd, 1H, J=6.0, J=2.4), 6.62 (d, 1H, J=2.1), 6.45 (dd, 1H, J=8.7, J=2.2), 5.39 (brs, 2H), 4.49 (d, 2H, J=4.0), 3.92 (t, 2H, J=8.2), 3.30 (m, 2H), 3.06 (t, 2H, J=8.1), 2.96 (t, 2H, J=7.5).

MS (ES+) m/z 385 (M+1).

Example B5

Preparation of Compound 5

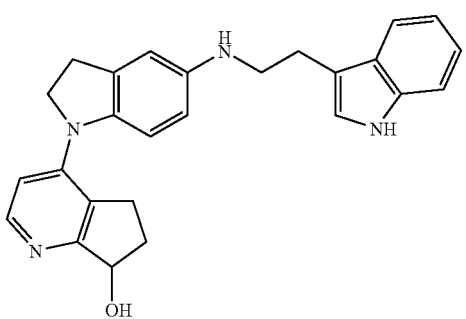

At 0° C. under argon, lithium aluminum hydride (14 mg, 0.00036 mol) was added to a solution of intermediate 7 (74 mg, 0.00036 mol) in THF (1 ml). The mixture was stirred at 0° C. for 1 hour, quenched with a 5% solution of potassium hydrogen sulfate, and extracted twice with EtOAc. The organic layer was separated, washed with brine, dried (MgSO$_4$), filtered, and the solvent was evaporated, to give the indole-3-yl acetaldehyde as an orange oil.

To a mixture of intermediate 13 (100 mg, 0.00037 mol) and sodium cyanoborohydride (33 mg, 0.00052 mol) in MeOH (1.5 ml) and acetic acid (2 drops), was added dropwise a solution of the previous aldehyde (57 mg, 0.00036 mol) in MeOH (0.5 ml). The reaction mixture was stirred at room temperature for 18 hours. The reaction was quenched with a saturated solution of sodium hydrogen carbonate and extracted twice with EtOAc. The organic layer was separated, washed with brine, dried (MgSO$_4$), filtered, and the solvent was evaporated. The residue was purified by column chromatography over silica gel (40-63 μm) (eluent: DCM/MeOH 100/0 to 90/10). The pure fractions were collected and the solvent was evaporated, yielding 79 mg (52%) of compound 5 as a yellow foam.

$^1$H NMR (300 MHz, CDCl$_3$) δ 8.37 (brs, 1H), 8.15 (d, 1H, J=5.8), 7.63 (d, 1H, J=7.8), 7.37 (d, 1H, J=7.1), 7.21 (dt, 1H, J=7.6, J=1.2), 7.12 (dt, 1H, J=7.6, J=1.1), 7.07 (m, 2H), 6.83 (d, 1H, J=8.5), 6.56 (d, 1H, J=2.0), 6.40 (dd, 1H, J=8.5, J=2.3), 5.22 (t, 1H, J=6.7), 4.19 (brs, 1H), 4.04 (m, 3H), 3.44 (t, 2H, J=6.7), 3.06 (m, 5H), 2.83 (m, 1H), 2.54 (m, 1H), 2.08 (m, 1H).

MS (ES+) m/z 411 (M+1).

Example B6

Preparation of Compound 6

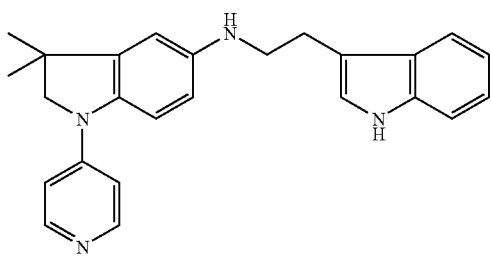

Intermediate 16 (0.001 mol) was added portionwise to a solution of lithium aluminum tetrahydride (0.002 mol) in THF (10 ml) under N$_2$ flow. The mixture was stirred and refluxed for 24 hours, poured out into ice water and filtered over celite. Celite was washed with EtOAc. The filtrate was extracted with EtOAc. The organic layer was separated, dried (MgSO$_4$), filtered and the solvent was evaporated. The residue (0.45 g) was purified by column chromatography over silica gel (10 μm) (eluent: DCM/MeOH/NH$_4$OH 95/5/0.5). The pure fractions were collected and the solvent was evaporated, yielding 0.042 g of compound 6.

$^1$H NMR (DMSO-d6) δ 1.28(6H,s), 2.95(2H,t,J=7.7Hz), 3.27-3.34(2H, m), 3.65(2H,s), 5.38 (1H,br,t, J=6.4Hz), 6.45 (1H,d,J=4Hz, 7.7Hz), 6.57(1H,d,J=4Hz), 6.96-7.02(3H m), 7.07(1H,t,J=7.7Hz), 7.15-7.5(3H,m), 7.35(1H,d,J=7.7Hz), 7.55(1H,d,J=7.7Hz), 8.22(1H,d,J=7.7Hz), 10.83(1H,br,s)

MS (ES+) m/z 383 (M+1), R$_t$=9.17, method A

Table F-1 lists the compounds that were prepared in one of the above examples.

TABLE F-1

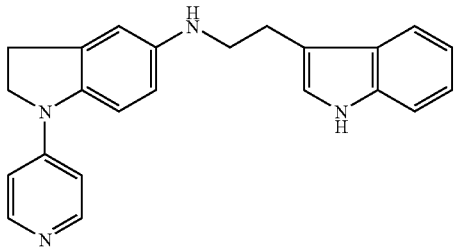

Co. No. 1; Ex. [B1]

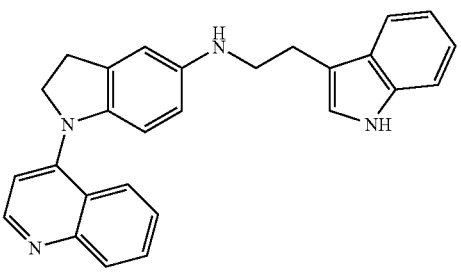

Co. No. 2; Ex. [B2]

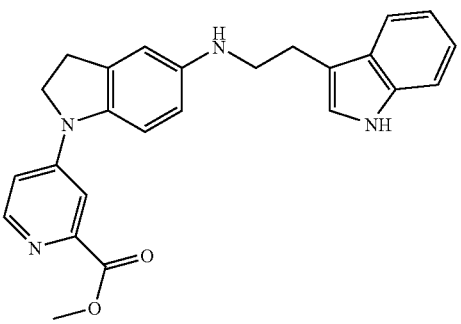

Co. No. 3; Ex. [B3]

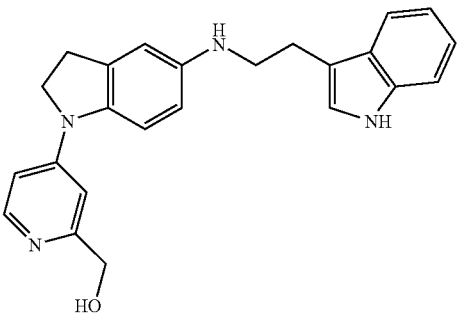

Co. No. 4; Ex. [B4]

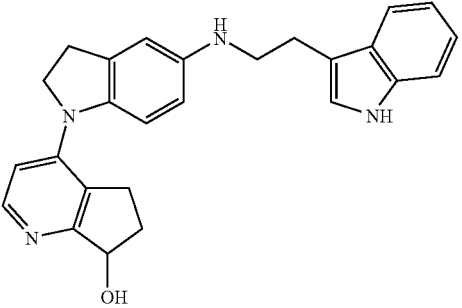

Co. No. 5; Ex. [B5]

TABLE F-1-continued

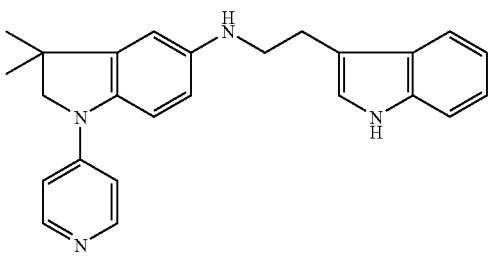

Co. No. 6; Ex. [B6]

C. Pharmacological Example

The capacity of the compounds to preserve p53 in A2780 cells was measured with the p53 enzyme linked immunosorbent assay. The p53 assay is a "sandwich" enzyme immunoassay employing two polyclonal antibodies. A polyclonal antibody, specific for the p53 protein, has been immobilized onto the surface of the plastic wells. Any p53 present in the sample to be assayed will bind to the capture antibody. The biotinylated detector polyclonal antibody also recognizes p53 protein, and will bind to any p53, which has been retained by the capture antibody. The detector antibody, in turn, is bond by horseradish peroxidase-conjugated streptavidin. The horseradish peroxidase catalyses the conversion of the chromogenic substrate o-phenylene diamine, the intensity of which is proportional to the amount of p53 protein bond to the plate. The colored reaction product is quantified using a spectrophotometer. Quantitation is achieved by the construction of a standard curve using known concentrations of purified recombinant HIS tagged p53 protein (see example C.1.).

Cellular activity of the compounds of formula (I) was determined on U87MG tumour cells using a colorimetric assay for cell toxicity or survival (see example C.2).

U87MG cells are human glioblastoma cells with wild type p53. In this cell line MDM2 tightly controls p53 expression.

C.1. p53 ELISA

A2780 cells (ATCC) were cultivated in RPMI 1640 supplemented with 10% fetal calf serum (FCS), 2 mM L-glutamine and gentamycin at 37° C. in a humidified incubator with 5% $CO_2$.

A2780 cells were seeded at 20.000 cells per well in a 96 well plate, cultured for 24 hours and treated with compound for 16 hours at 37° C. in a humidified incubator. After incubation, the cells were washed once with phosphate-buffered saline and 30 µl, per well, low salt RIPA buffer (20 mM tris, pH7.0, 0.5 mM EDTA, 1% Nonidet P40, 0.5% DOC, 0.05% SDS, 1 mM PMSF, 1 µg/ml aprotinin and 0.5 µ/ml leupeptin) was added. Plates were placed on ice for 30 minutes to complete the lysis. p53 protein was detected in de lysates by using the sandwich ELISA, described below.

High binding polystyrene EIA/RIA 96 well plates (Costar 9018) were coated with the capture antibody pAb1801 (Abeam ab28-100) at a concentration of 1 µg/ml in coating buffer (0.1 M $NaHCO_3$ pH8.2), 50 µl per well. The antibody was allowed to adhere overnight at 4° C. Coated plates were washed once with phosphate-buffered saline (PBS)/0.05% Tween 20 and 300 µl of blocking buffer (PBS, 1% bovine serum albumins (BSA)) was added, for an incubation period of 2 hours at room temperature. Dilutions of purified recombinant HIS tagged p53 protein, ranging from 3-200 ng/ml, were made in blocking buffer and used as standards.

Plates were washed twice with PBS 0.05% Tween 20 and blocking buffer or standards were added at 80 µl/well. To the standards, 20 µl of lysis buffer was added. The samples were added to the other wells at 20 µl lysate/well. After an overnight incubation at 4° C., plates were washed twice with PBS/0.05% Tween 20. Aliquots of 100 µl secondary polyclonal antibody p53(FL-393) (Tebubio, sc-6243) at a concentration of 1 µg/ml in blocking buffer were added to each well and allowed to adhere for 2 hours at room temperature. Plates were washed three times with PBS/0.05% Tween 20. Detection antibody anti-rabbit HRP (sc-2004, Tebubio) at 0.04 µg/ml in PBS/1% BSA was added and incubated for 1 hour at room temperature. Plates were washed three times with PBS/0.05% Tween 20 and 100 µl of substrate buffer was added (substrate buffer was prepared shortly before use by adding 1 tablet of 10 mg o-phenylene diamine (OPD) from Sigma and 125 µl 3% $H_2O_2$ to 25 ml OPD buffer: 35 mM citric acid, 66 mM $Na_2HPO_4$, pH5.6). After 5 to 10 minutes, colour reaction was stopped by adding 50 µl stop buffer (1 M $H_2SO_4$) per well. The absorbance at dual wavelengths of 490/655 nm was measured using a Biorad micro plate reader and the results were then analyzed.

For each experiment, controls (containing no drug) and a blank incubation (containing no cells or drugs) were run in parallel. The blank value was subtracted from all control and sample values. For each sample, the value of p53 (in absorbance units) was expressed as the percentage of the value for p53 present in the control. Percentage preservation higher than 140% was defined as significant. Herein the effects of test compounds are expressed as the lowest dose giving at least 140% of the value for p53 present in the control (LAD) (see table F-2).

C.2. Proliferation Assay

All compounds tested were dissolved in DMSO and further dilutions were made in culture medium. Final DMSO concentrations never exceeded 0.1% (v/v) in cell proliferation assays. Controls contained U87MG cells and DMSO without compound and blanks contained DMSO but no cells.

U87MG cells were seeded in 96-well cell culture plates at 3000 cells/well/100 µl. 24 hours later, medium was changed and compound and/or solvent were added to a final volume of 200 µl. Following 4 days of incubation, medium was replaced by 200 µl fresh medium and cell growth was assessed using a MTT-based assay. Therefore, 25 µl of the MTT solution (0.5% MTT research grade from Serva in phosphate-buffered saline) was added to each well and the cells were further incubated for 2 hours at 37° C. The medium was then carefully aspirated and the blue MTT-formazan product was dissolved by adding to each well 25 µl 0.1M glycin and 100 µl DMSO. The plates were shaken for another 10 min on a micro plate shaker before reading absorbance at 540 nm by a Biorad micro plate reader.

Within an experiment, the results for each experimental condition are the mean of 3 replicate wells. For initial screening purposes, compounds were tested at a single fixed concentration of $10^{-5}$ M. For active compounds, the experiments were repeated to establish full concentration-response curves. For each experiment, controls (containing no drug) and a blank incubation (containing no cells or drugs) were run in parallel. The blank value was subtracted from all control and sample values. For each sample, the mean value for cell growth (in absorbance units) was expressed as a percentage of the mean value for cell growth of the control. When appropriate, $IC_{50}$-values (concentration of the drug, needed to reduce cell growth to 50% of the control) were computed using probit analysis for graded data (Finney, D. J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value) (see table F-2).

In some of the experiments the proliferation assay was adapted for and used in 384-well culture plates (see table F-2).

TABLE F-2

Table F-2 lists the results of the compounds that were tested according to example C.1 and C.2.

| Co No | A2780 p53-elisa LAD | cell proliferation $pIC_{50}$ 384 well | cell proliferation $pIC_{50}$ 96 well |
|---|---|---|---|
| 1 | 1.0E−07 | | 8.00 |
| 2 | 1.0E−06 | | 5.77 |
| 4 | 3.0E−07 | | 6.80 |
| 3 | 1.0E−06 | | 5.38 |
| 5 | 3.0E−07 | | 6.53 |
| 6 | 3.0E−06 | 6.53 | |

D. Composition Example

Film-coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I), (I)

a N-oxide form, an addition salt or a stereochemically isomeric form thereof, wherein m is 0, and a direct bond is intended;

n is 2, p is 1, t is 0, and a direct bond is intended;

is $—CR^8=C<$ and the dotted line is a bond, wherein $R^8$ is hydrogen or $C_{1-6}$alkyl;

$R^1$ and $R^2$ are hydrogen;

$R^3$ and $R^4$ are hydrogen;

$R^5$ is hydrogen;

$R^6$ and $R^7$ are each independently selected from hydrogen or $C_{1-6}$alkyl; Z is a radical selected from (a-1)

(a-2)

(a-4)

$R^{10}$ and $R^{11}$ are each independently selected from hydrogen, hydroxy, $C_{1-6}$alkyloxycarbonyl or hydroxy$C_{1-6}$alkyl.

2. A compound selected from the group consisting of:

Co. No. 1

-continued

Co. No. 4

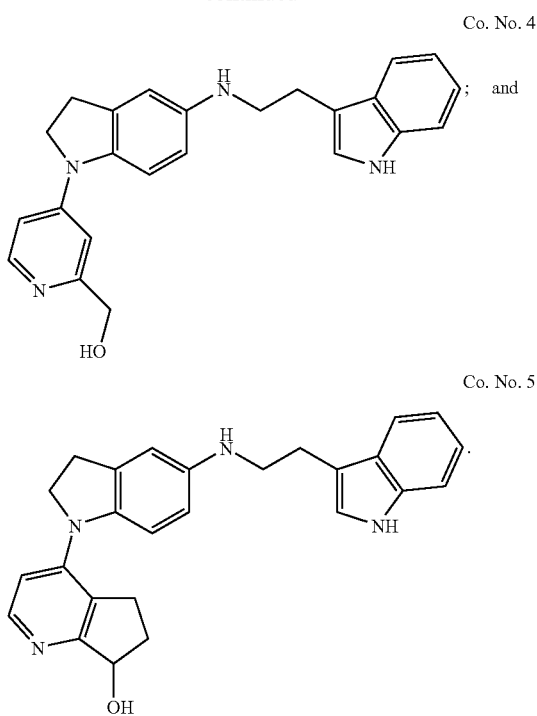

3. A pharmaceutical composition comprising pharmaceutically acceptable carriers and a compound as claimed in claim 1.

4. A process for preparing a compound as claimed in claim 1, said process comprising the steps of:

a) reacting an intermediate of formula (II) with an intermediate of formula (III) wherein W is an appropriate leaving group,

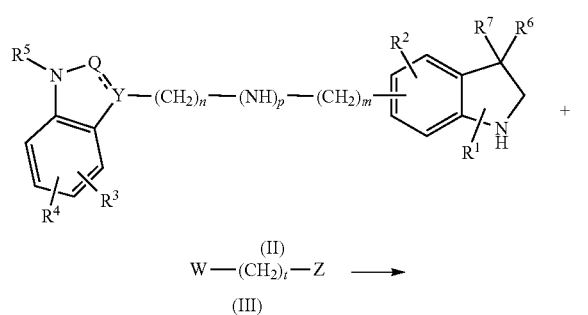

(II)

W—(CH$_2$)$_t$—Z ⟶

(III)

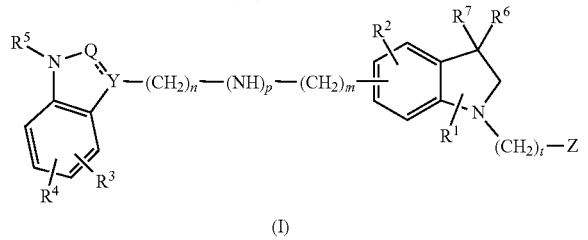

(I)

b) converting an intermediate of formula (IV) into compounds of formula (I), wherein p is 1, herein referred to as compounds of formula (I-a), in the presence of lithium aluminium hydride in a suitable solvent, or

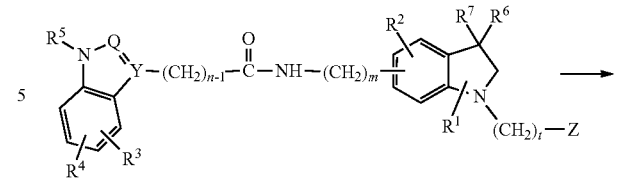

(IV)

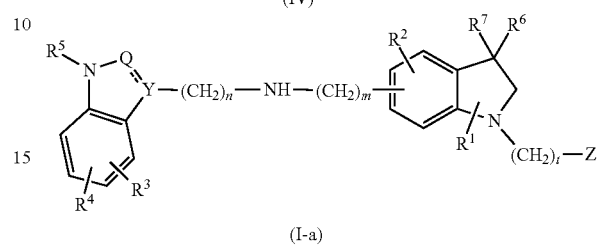

(I-a)

c) reacting an appropriate carboxaldehyde of formula (VI), with an intermediate of formula (V), in the presence of an appropriate reagent, in a suitable solvent,

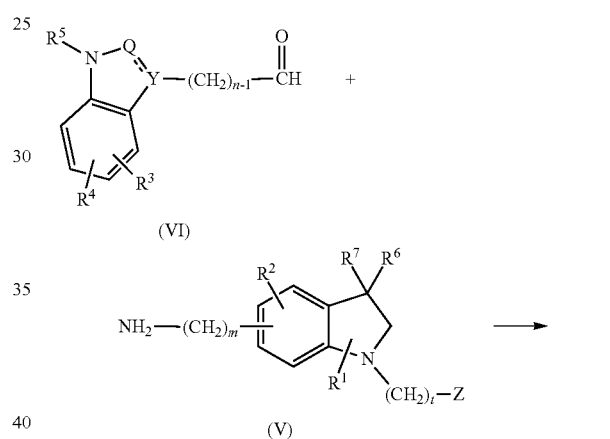

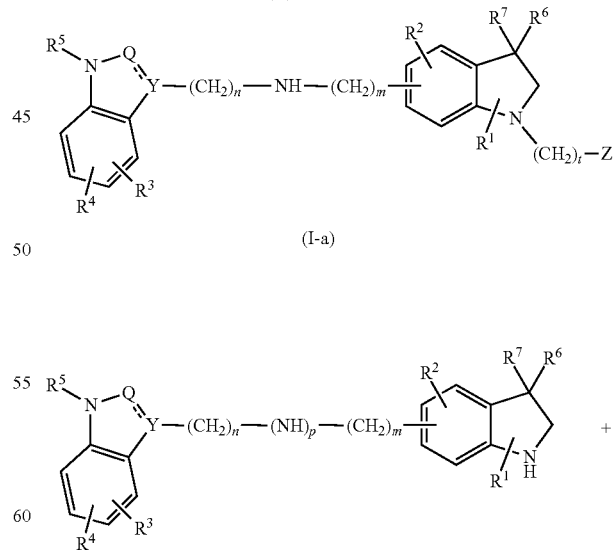

(I-a)

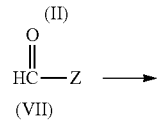

(VII)

-continued
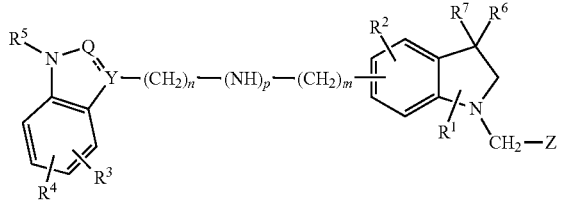
(I-b)
5. A pharmaceutical composition comprising pharmaceutically acceptable carriers and a compound as claimed in claim 2.
6. A compound according to claim 1 wherein
   $R^6$ and $R^7$ are each independently hydrogen;
   Z is a radical selected from (a-2) or (a-4); and
   $R^{10}$ and $R^{11}$ are each independently selected from hydrogen, hydroxy, or hydroxyC$_{1-6}$alkyl.
* * * * *